US012773257B2

(12) United States Patent
Dickerson et al.

(10) Patent No.: US 12,773,257 B2
(45) Date of Patent: Oct. 27, 2026

(54) KNIFE HOUSING FOR SURGICAL TOOL END EFFECTORS

(71) Applicant: Cilag GmbH International, Zug (CH)

(72) Inventors: Benjamin D. Dickerson, Cincinnati, OH (US); Jason A. Hill, Loveland, OH (US)

(73) Assignee: Cilag GmbH International, Zug (CH)

( * ) Notice: Subject to any disclaimer, the term of this patent is extended or adjusted under 35 U.S.C. 154(b) by 658 days.

(21) Appl. No.: 18/177,035

(22) Filed: Mar. 1, 2023

(65) Prior Publication Data

US 2024/0293171 A1 Sep. 5, 2024

(51) Int. Cl.

*A61B 18/14* (2006.01)
*A61B 17/29* (2006.01)
*A61B 18/00* (2006.01)
*A61B 34/30* (2016.01)

(52) U.S. Cl.

CPC .. *A61B 18/1445* (2013.01); *A61B 2017/2926* (2013.01); *A61B 2018/0063* (2013.01); *A61B 2018/1455* (2013.01); *A61B 2034/302* (2016.02)

(58) Field of Classification Search

CPC .......... A61B 18/1445; A61B 2034/302; A61B 2017/2926; A61B 2018/0063; A61B 2018/1455

See application file for complete search history.

(56) References Cited

U.S. PATENT DOCUMENTS

2006/0079889 A1 4/2006 Scott
2007/0244511 A1* 10/2007 Weizman ............... A61B 10/06 606/205
2008/0091189 A1 4/2008 Carlton
2010/0179540 A1* 7/2010 Marczyk ............ A61B 18/1445 606/41
2011/0077649 A1* 3/2011 Kingsley ............ A61B 18/1445 606/205
2011/0106145 A1 5/2011 Jeong
2011/0276048 A1 11/2011 Kerr et al.
2013/0331826 A1 12/2013 Steege (Continued)

FOREIGN PATENT DOCUMENTS

WO 2020/192847 A2 10/2020

OTHER PUBLICATIONS

International Preliminary Report on Patentability for PCT/IB2024/051912, issued Aug. 28, 2025, 6 pages.

(Continued)

*Primary Examiner* — Joanne M Rodden
*Assistant Examiner* — Bo Ouyang
(74) *Attorney, Agent, or Firm* — Vorys, Sater, Seymour and Pease LLP

(57) ABSTRACT

An end effector for a surgical tool includes opposing first and second jaws rotatably coupled to each other at a jaw pivot axis, a knife slot defined in one or both of the first and second jaws, a knife coupled to a distal end of a drive rod and longitudinally extendable into the knife slot, and a knife housing pivotably coupled between the first and second jaws at the jaw pivot axis and defining a cavity sized to receive the knife. The drive rod is actuatable to move the knife between a stowed position, where the knife is received within the cavity, and an extended position, where the knife is extended out of the cavity and into the knife slot.

20 Claims, 16 Drawing Sheets

(56) References Cited

U.S. PATENT DOCUMENTS

| | | | | |
|---|---|---|---|---|
| 2014/0188101 | A1* | 7/2014 | Bales, Jr. | A61B 18/1445 606/33 |
| 2014/0221999 | A1* | 8/2014 | Cunningham | A61B 18/1442 606/52 |
| 2014/0353869 | A1 | 12/2014 | Goodman et al. | |
| 2015/0150635 | A1 | 6/2015 | Kilroy et al. | |
| 2015/0297288 | A1 | 10/2015 | Joseph | |
| 2015/0305797 | A1 | 10/2015 | Hassoun | |
| 2017/0202608 | A1 | 7/2017 | Shelton, IV et al. | |
| 2017/0215941 | A1 | 8/2017 | Kazuno | |
| 2020/0305965 | A1* | 10/2020 | Pham | A61B 17/29 |
| 2021/0022819 | A1 | 1/2021 | Duque et al. | |
| 2022/0226050 | A1 | 7/2022 | Johnson et al. | |
| 2022/0226059 | A1 | 7/2022 | Beckman et al. | |
| 2024/0293170 | A1 | 9/2024 | Dickerson et al. | |

OTHER PUBLICATIONS

International Search Report and Written Opinion, received for PCT Application No. PCT/IB2024/051912, mailed on May 10, 2024, 13 pages.

* cited by examiner

KNIFE HOUSING FOR SURGICAL TOOL END EFFECTORS

BACKGROUND

Minimally invasive surgical (MIS) instruments are often preferred over traditional open surgical devices due to reduced post-operative recovery time and minimal scarring. Laparoscopic surgery is one type of MIS procedure in which one or more small incisions are formed in the abdomen of a patient and a trocar is inserted through the incision to form a pathway that provides access to the abdominal cavity. Through the trocar, a variety of instruments and surgical tools can be introduced into the abdominal cavity. The instruments and tools introduced into the abdominal cavity via the trocar can be used to engage and/or treat tissue in a number of ways to achieve a diagnostic or therapeutic effect.

Various robotic systems have recently been developed to assist in MIS procedures. Robotic systems can allow for more instinctive hand movements by maintaining natural eye-hand axis. Robotic systems can also allow for more degrees of freedom in movement by including an articulable "wrist" joint that creates a more natural hand-like articulation. In such systems, an end effector positioned at the distal end of the instrument can be articulated (moved) using a cable driven motion system having one or more drive cables that extend through the wrist joint. A user (e.g., a surgeon) is able to remotely operate the end effector by grasping and manipulating in space one or more controllers that communicate with a tool driver coupled to the surgical instrument. User inputs are processed by a computer system incorporated into the robotic surgical system, and the tool driver responds by actuating the cable driven motion system. Moving the drive cables articulates the end effector to desired angular positions and configurations.

One type of end effector is a combination vessel sealer and tissue grasper that has opposing jaws capable of closing down and "grasping" onto tissue. Once tissue is properly grasped, a knife can be advanced distally within a knife slot to transect the grasped tissue, and electrical energy may be applied (prior to, during, or after transection) to the end effector to seal and cauterize the transected tissue.

It is desirable to improve vessel sealers and their operation to make minimally invasive surgeries more effective and efficient.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

DETAILED DESCRIPTION

The present disclosure is related to robotic surgical systems and, more particularly, to improved designs for tissue grasper end effectors.

One example end effector includes a first jaw having a first electrode and a first insulator secured thereto, and a second jaw having a second electrode and a second insulator secured thereto, the first and second jaws being pivotable between open and closed positions. A knife slot may be cooperatively defined in the first and second jaws and define a diamond-shape cross-section when the first and second jaws are in the closed position. A knife may be extendable into the knife slot and longitudinally movable within the knife slot.

A surgical tool disclosed herein includes a wrist including a proximal clevis and a distal clevis rotatably mountable to the proximal clevis at a first pivot axis, and an end effector rotatably coupled to the distal clevis at a second pivot axis, the end effector including opposing first and second jaws rotatably coupled to each other at a jaw pivot axis. The jaw pivot axis may be parallel to the second pivot axis and orthogonal to the first pivot axis, and a longitudinal axis of the end effector may be perpendicular to and intersects the jaw pivot axis.

Another example end effector includes opposing first and second jaws rotatably coupled to each other at a jaw pivot axis, a knife slot defined in one or both of the first and second jaws, and a knife coupled to a distal end of a drive rod and longitudinally extendable into the knife slot. A knife housing may be pivotably coupled between the first and second jaws at the jaw pivot axis and define a cavity sized to receive the knife. The drive rod may be actuatable to move the knife between a stowed position, where the knife is received within the cavity, and an extended position, where the knife is extended out of the cavity and into the knife slot.

Figure 1:
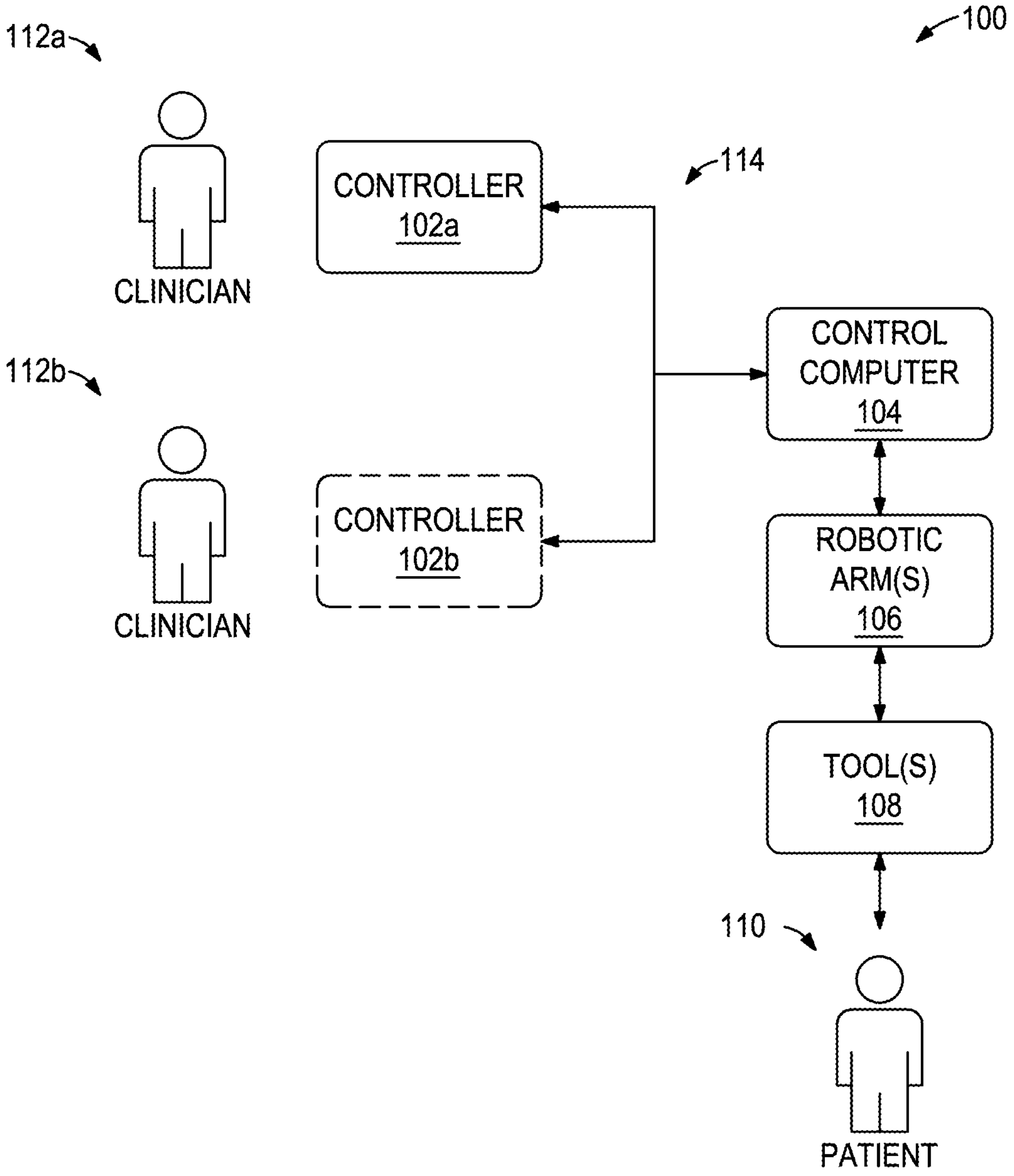
FIG. 1 is a block diagram of an example robotic surgical system that may incorporate some or all of the principles of the present disclosure.

FIG. 1 is a block diagram of an example robotic surgical system 100 that may incorporate some or all of the principles of the present disclosure. As illustrated, the system 100 can include at least one set of user input controllers 102*a* and at least one control computer 104. The control computer 104 may be mechanically and/or electrically coupled to a robotic manipulator and, more particularly, to one or more robotic arms 106 (alternately referred to as "tool drivers"). In some embodiments, the robotic manipulator may be included in or otherwise mounted to an arm cart capable of making the system portable. Each robotic arm 106 may include and otherwise provide a location for mounting one or more surgical instruments or tools 108 for performing various surgical tasks on a patient 110. Operation of the robotic arms 106 and associated tools 108 may be directed by a clinician 112*a* (e.g., a surgeon) from the user input controller 102*a*.

In some embodiments, a second set of user input controllers 102*b* (shown in dashed line) may be operated by a second clinician 112*b* to direct operation of the robotic arms 106 and tools 108 via the control computer 104 and in conjunction with the first clinician 112*a*. In such embodiments, for example, each clinician 112*a,b* may control different robotic arms 106 or, in some cases, complete control of the robotic arms 106 may be passed between the clinicians 112*a,b* as needed. In some embodiments, additional robotic manipulators having additional robotic arms may be utilized during surgery on the patient 110, and these additional robotic arms may be controlled by one or more of the user input controllers 102*a,b*.

The control computer 104 and the user input controllers 102*a,b* may be in communication with one another via a communications link 114, which may be any type of wired or wireless telecommunications means configured to carry a variety of communication signals (e.g., electrical, optical, infrared, etc.) according to any communications protocol. In some applications, for example, there is a tower with ancillary equipment and processing cores designed to drive the robotic arms 106.

The user input controllers 102*a,b* generally include one or more physical controllers that can be grasped by the clinicians 112*a,b* and manipulated in space while the surgeon views the procedure via a stereo display. The physical controllers generally comprise manual input devices movable in multiple degrees of freedom, and which often include an actuatable handle for actuating the surgical tool(s) 108, for example, for opening and closing opposing jaws, applying an electrical potential (current) to an electrode, or the like. The control computer 104 can also include an optional feedback meter viewable by the clinicians 112*a,b* via a display to provide a visual indication of various surgical instrument metrics, such as the amount of force being applied to the surgical instrument (i.e., a cutting instrument or dynamic clamping member).

Figures 2, 3:
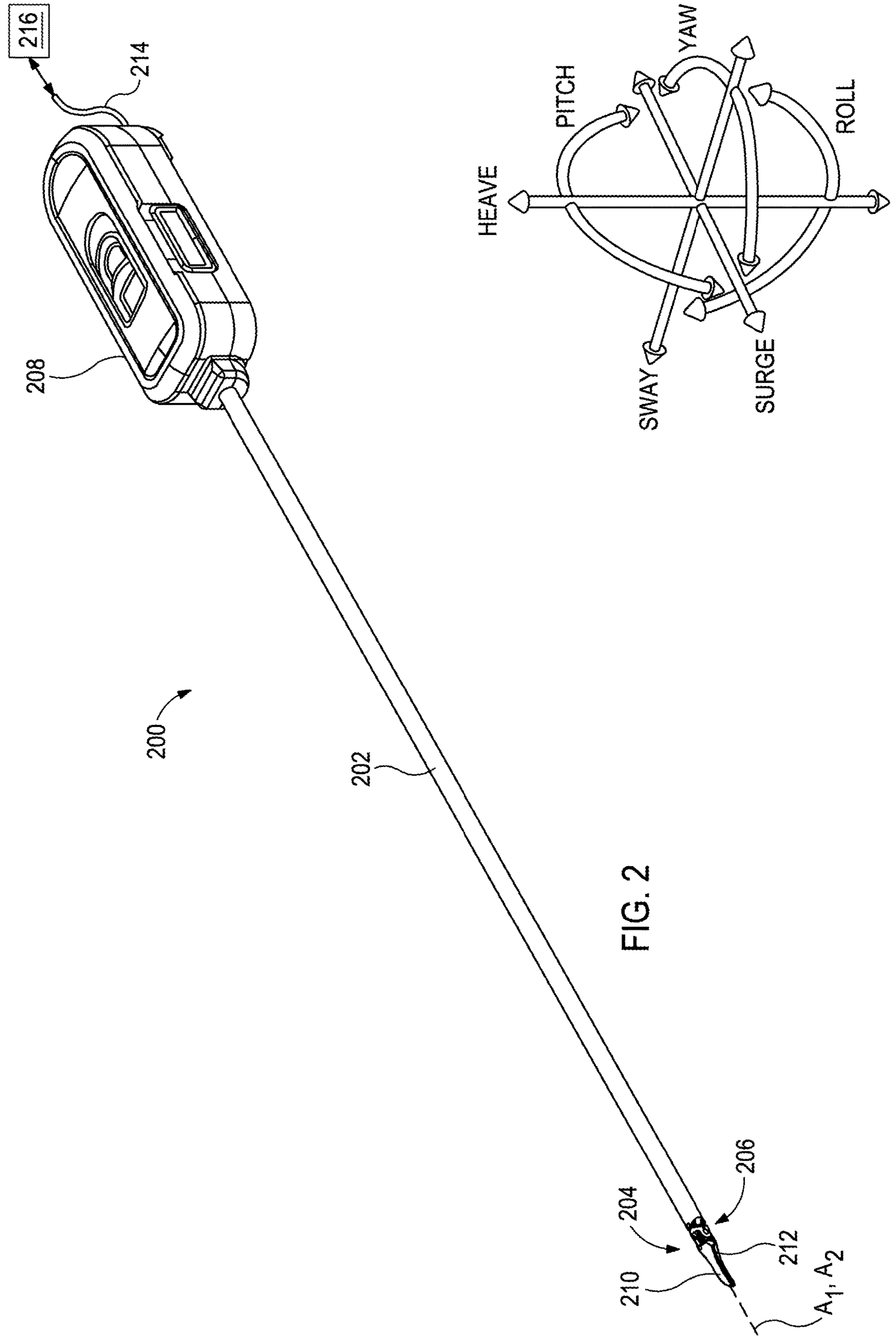
FIG. 2 is an isometric side view of an example surgical tool that may incorporate some or all of the principles of the present disclosure.
FIG. 3 illustrates potential degrees of freedom in which the wrist of the surgical tool of FIG. 2 may be able to articulate (pivot) and translate.

FIG. 2 is an isometric side view of an example surgical tool 200 that may incorporate some or all of the principles of the present disclosure. The surgical tool 200 may be the same as or similar to the surgical tool(s) 108 of FIG. 1 and, therefore, may be used in conjunction with a robotic surgical system, such as the robotic surgical system 100 of FIG. 1. Accordingly, the surgical tool 200 may be designed to be releasably coupled to a tool driver included in the robotic surgical system 100. In other embodiments, however, aspects of the surgical tool 200 may be adapted for use in a manual or hand-operated manner, without departing from the scope of the disclosure.

As illustrated, the surgical tool 200 includes an elongated shaft 202, an end effector 204, a wrist 206 (alternately referred to as a "wrist joint" or an "articulable wrist joint") that couples the end effector 204 to the distal end of the shaft 202, and a drive housing 208 coupled to the proximal end of the shaft 202. In applications where the surgical tool is used in conjunction with a robotic surgical system (e.g., the robotic surgical system 100 of FIG. 1), the drive housing 208 can include coupling features that releasably couple the surgical tool 200 to the robotic surgical system.

The terms "proximal" and "distal" are defined herein relative to a robotic surgical system having an interface configured to mechanically and electrically couple the surgical tool 200 (e.g., the housing 208) to a robotic manipulator. The term "proximal" refers to the position of an element closer to the robotic manipulator and the term "distal" refers to the position of an element closer to the end effector 204 and thus further away from the robotic manipulator. Alternatively, in manual or hand-operated applications, the terms "proximal" and "distal" are defined herein relative to a user, such as a surgeon or clinician. The term "proximal" refers to the position of an element closer to the user and the term "distal" refers to the position of an element closer to the end effector 204 and thus further away from the user. Moreover, the use of directional terms such as above, below, upper, lower, upward, downward, left, right, and the like are used in relation to the illustrative embodiments as they are depicted in the figures, the upward or upper direction being toward the top of the corresponding figure and the downward or lower direction being toward the bottom of the corresponding figure.

During use of the surgical tool 200, the end effector 204 is configured to move (pivot) relative to the shaft 202 at the wrist 206 to position the end effector 204 at desired orientations and locations relative to a surgical site. To accomplish this, the housing 208 includes (contains) various drive inputs and mechanisms (e.g., gears, actuators, etc.) designed to control operation of various features associated with the end effector 204 (e.g., clamping, firing, cutting, rotation, articulation, etc.). In at least some embodiments, the shaft 202, and hence the end effector 204 coupled thereto, is configured to rotate about a longitudinal axis $A_1$ of the shaft 202. In such embodiments, at least one of the drive inputs included in the housing 208 is configured to control rotational movement of the shaft 202 about the longitudinal axis $A_1$.

The shaft 202 is an elongate member extending distally from the housing 208 and has at least one lumen extending therethrough along its axial length. In some embodiments, the shaft 202 may be fixed to the housing 208, but could alternatively be rotatably mounted to the housing 208 to allow the shaft 202 to rotate about the longitudinal axis $A_1$. In yet other embodiments, the shaft 202 may be releasably coupled to the housing 208, which may allow a single housing 208 to be adaptable to various shafts having different end effectors.

The end effector 204 can exhibit a variety of sizes, shapes, and configurations. In the illustrated embodiment, the end effector 204 comprises a combination tissue grasper and vessel sealer that include opposing jaws 210, 212 configured to move (articulate) between open and closed positions. As will be appreciated, however, the opposing jaws 210, 212 may alternatively form part of other types of end effectors such as, but not limited to, a surgical scissors, a clip applier, a needle driver, a babcock including a pair of opposed grasping jaws, bipolar jaws (e.g., bipolar Maryland grasper, forceps, a fenestrated grasper, etc.), etc. One or both of the jaws 210, 212 may be configured to pivot to articulate the end effector 204 between the open and closed positions.

FIG. 3 illustrates the potential degrees of freedom in which the wrist 206 may be able to articulate (pivot). The wrist 206 can have any of a variety of configurations. In general, the wrist 206 comprises a joint configured to allow pivoting movement of the end effector 204 relative to the shaft 202. The degrees of freedom of the wrist 206 are represented by three translational variables (i.e., surge, heave, and sway), and by three rotational variables (i.e., Euler angles or roll, pitch, and yaw). The translational and rotational variables describe the position and orientation of the end effector 204 with respect to a given reference Cartesian frame. As depicted in FIG. 3, "surge" refers to forward and backward translational movement, "heave" refers to translational movement up and down, and "sway" refers to translational movement left and right. With regard to the rotational terms, "roll" refers to tilting side to side, "pitch" refers to tilting forward and backward, and "yaw" refers to turning left and right.

The pivoting motion can include pitch movement about a first axis of the wrist 206 (e.g., X-axis), yaw movement about a second axis of the wrist 206 (e.g., Y-axis), and combinations thereof to allow for 360° rotational movement of the end effector 204 about the wrist 206. In other applications, the pivoting motion can be limited to movement in a single plane, e.g., only pitch movement about the first axis of the wrist 206 or only yaw movement about the second axis of the wrist 206, such that the end effector 204 moves only in a single plane.

Referring again to FIG. 2, the surgical tool 200 may also include a plurality of drive cables (obscured in FIG. 2) that form part of a cable driven motion system configured to facilitate movement and articulation of the end effector 204 relative to the shaft 202. Moving (actuating) one or more of the drive cables moves the end effector 204 between an unarticulated position and an articulated position. The end effector 204 is depicted in FIG. 2 in the unarticulated position where a longitudinal axis $A_2$ of the end effector 204 is substantially aligned with the longitudinal axis $A_1$ of the shaft 202, such that the end effector 204 is at a substantially zero angle relative to the shaft 202. Due to factors such as manufacturing tolerance and precision of measurement devices, the end effector 204 may not be at a precise zero angle relative to the shaft 202 in the unarticulated position, but nevertheless be considered "substantially aligned" thereto. In the articulated position, the longitudinal axes $A_1$, $A_2$ would be angularly offset from each other such that the end effector 204 is at a non-zero angle relative to the shaft 202.

In some embodiments, the surgical tool 200 may be supplied with electrical power (current) via a power cable 214 coupled to the housing 208. In other embodiments, the power cable 214 may be omitted and electrical power may be supplied to the surgical tool 200 via an internal power source, such as one or more batteries or fuel cells. In such embodiments, the surgical tool 200 may alternatively be characterized and otherwise referred to as an "electrosurgical instrument" capable of providing electrical energy to the end effector 204.

The power cable 214 may place the surgical tool 200 in electrical communication with a generator 216 that supplies energy, such as electrical energy (e.g., radio frequency energy), ultrasonic energy, microwave energy, heat energy, or any combination thereof, to the surgical tool 200 and, more particularly, to the end effector 204. Accordingly, the generator 216 may comprise a radio frequency (RF) source, an ultrasonic source, a direct current source, and/or any other suitable type of electrical energy source that may be activated independently or simultaneously.

In applications where the surgical tool 200 is configured for bipolar operation, the power cable 214 will include a supply conductor and a return conductor. Current can be supplied from the generator 216 to an active (or source) electrode located at the end effector 204 via the supply conductor, and current can flow back to the generator 216 via a return electrode located at the end effector 204 via the return conductor. In the case of a bipolar grasper with opposing jaws, for example, the jaws serve as the electrodes where the proximal end of the jaws are isolated from one another and the inner surface of the jaws (i.e., the area of the jaws that grasp tissue) apply the current in a controlled path through the tissue. In applications where the surgical tool 200 is configured for monopolar operation, the generator 216 transmits current through a supply conductor to an active electrode located at the end effector 204, and current is returned (dissipated) through a return electrode (e.g., a grounding pad) separately coupled to a patient's body.

Figure 4A:
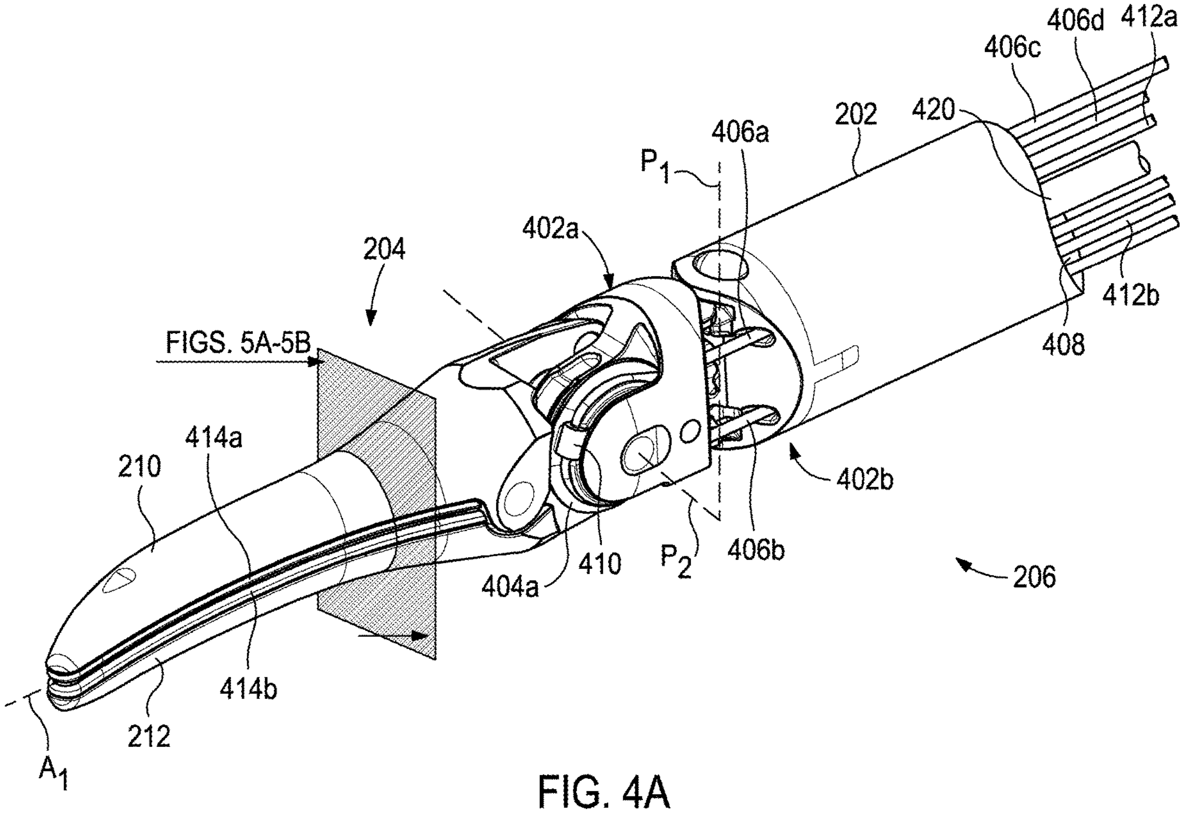
FIG. 4A is an enlarged isometric view of the distal end of the surgical tool of FIG. 2.

FIG. 4A is an enlarged isometric view of the distal end of the surgical tool 200. More specifically, FIG. 4A depicts an enlarged view of the end effector 204 and the wrist 206, with the jaws 210, 212 of the end effector 204 in the closed position. The wrist 206 operatively couples the end effector 204 to the shaft 202. In some embodiments, however, a shaft adapter may be directly coupled to the wrist 206 and otherwise interpose the shaft 202 and the wrist 206. Accordingly, the wrist 206 may be operatively coupled to the shaft 202 either through a direct coupling engagement where the wrist 206 is directly coupled to the distal end of the shaft 202, or an indirect coupling engagement where a shaft adapter interposes the wrist 206 and the distal end of the shaft 202. As used herein, the term "operatively couple" refers to a direct or indirect coupling engagement between two components.

To operatively couple the end effector 204 to the shaft 202, the wrist 206 includes a first or "distal" clevis 402*a* and a second or "proximal" clevis 402*b*. The clevises 402*a,b* may alternatively be referred to as "articulation joints" or "linkages." As described herein, the clevises 402*a,b* are operatively coupled to facilitate articulation of the wrist 206 relative to the shaft 202, thereby allowing the end effector 204 to articulate in yaw, pitch, or a combination of both yaw and pitch.

As illustrated, the proximal end of the distal clevis 402*a* may be rotatably mounted to the distal end of the proximal clevis 402*b* at a first pivot axis $P_1$ of the wrist 206. First and second pulleys 404*a* and 404*b* (only the first pulley 404*a* is visible in FIG. 4A; see FIG. 4B) may be rotatably mounted to the distal end of the distal clevis 402*a* at a second pivot axis $P_2$ of the wrist 206. The first pivot axis $P_1$ is substantially perpendicular (orthogonal) to the longitudinal axis $A_1$ of the shaft 202, and the second pivot axis $P_2$ is substantially perpendicular (orthogonal) to both the longitudinal axis $A_1$ and the first pivot axis $P_1$. Movement of the end effector 204 about the first pivot axis $P_1$ provides "yaw" articulation of the wrist 206, and movement about the second pivot axis $P_2$ provides "pitch" articulation of the wrist 206.

A plurality of drive members, shown as drive members 406*a*, 406*b*, 406*c*, and 406*d*, extend longitudinally within a lumen 408 defined by the shaft 202 (or a shaft adaptor) and extend at least partially through the wrist 206. The drive members 406*a-d* may form part of the actuation systems housed within the drive housing 208 (FIG. 2), and may comprise cables, bands, lines, cords, wires, woven wires, ropes, strings, twisted strings, elongate members, belts, shafts, flexible shafts, drive rods, or any combination thereof. The drive members 406*a-d* can be made from a variety of materials including, but not limited to, a metal (e.g., tungsten, stainless steel, nitinol, etc.) a polymer (e.g., ultra-high molecular weight polyethylene), a synthetic fiber (e.g., KEVLAR®, VECTRAN®, etc.), an elastomer, or any combination thereof. While four drive members 406*a-d* are depicted in FIG. 4A, more or less than four may be employed, without departing from the scope of the disclosure.

The drive members 406*a-d* extend proximally from the end effector 204 and the wrist 206 toward the drive housing 208 (FIG. 2) where they are operatively coupled to various actuation mechanisms or devices that facilitate longitudinal movement (translation) of the drive members 406*a-d* within the lumen 408. Selective actuation of the drive members 406*a-d* applies tension (i.e., pull force) to the given drive member 406*a-d* in the proximal direction, which urges the given drive member 406*a-d* to translate longitudinally within the lumen 408.

Figure 4B:
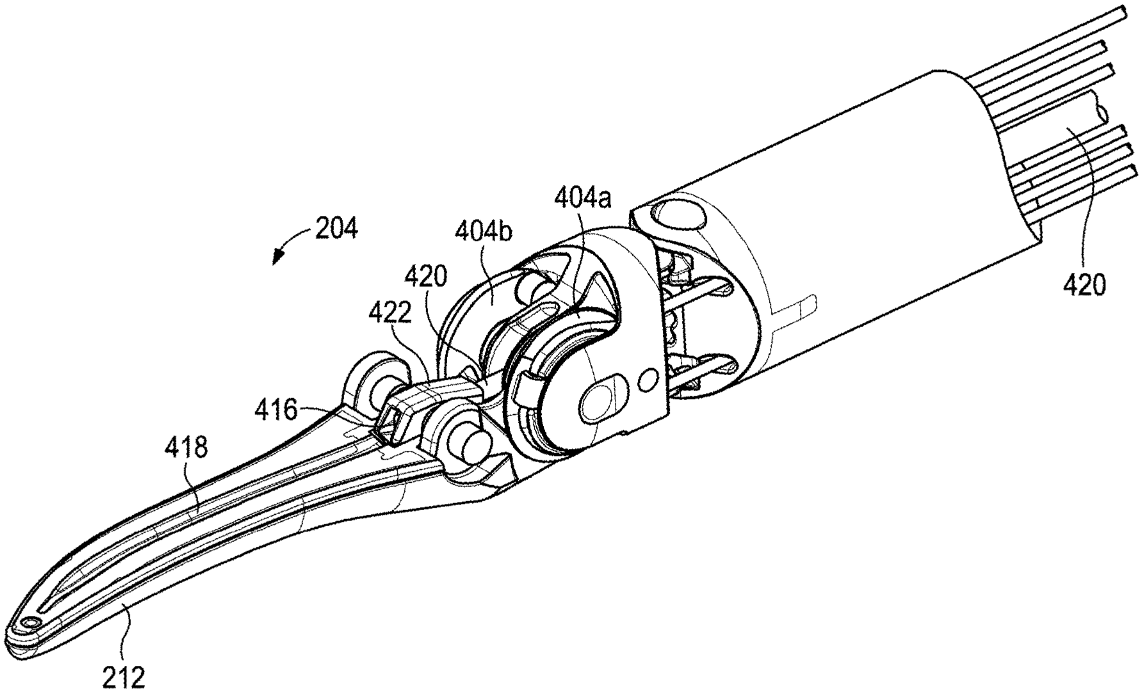
FIG. 4B an enlarged isometric view of the end effector of FIG. 4A, with one of the jaws removed.

In the illustrated embodiment, the drive members 406*a-d* each extend longitudinally through the proximal clevis 402*b*, and the distal end of each drive member 406*a-d* terminates at the first or second pulleys 404*a,b*, thus operatively coupling each drive member 406*a-d* to the end effector 204. In some embodiments, the distal ends of the first and second drive members 406*a,b* may be coupled to each other and terminate at the first pulley 404*a*, and the distal ends of the third and fourth drive members 406*c,d* may be coupled to each other and terminate at the second pulley 404*b* (FIG. 4B). In at least one embodiment, the distal ends of the first and second drive members 406*a,b* and the distal ends of the third and fourth drive members 406*c,d* may each be coupled together at a corresponding ball crimp 410 (only one shown) mounted to the first or second pulley 404*a,b*, respectively.

In the illustrated embodiment, the drive members 406*a-d* operate "antagonistically". More specifically, when the first drive member 406*a* is actuated (moved in tension), the second drive member 406*b* naturally follows as coupled to the first drive member 406*a*, and vice versa. Similarly, when the third drive member 406*c* is actuated (moved in tension), the fourth drive member 406*d* naturally follows as coupled to the third drive member 406*c*, and vice versa. Antagonistic operation of the drive members 406*a-d* can open or close the jaws 210, 212 and can further cause the end effector 204 to articulate at the wrist 206. More specifically, selective actuation of the drive members 406*a-d* in known configurations or coordination can cause the end effector 204 to articulate about one or both of the pivot axes $P_1$, $P_2$, thus facilitating articulation of the end effector 204 in both pitch and yaw directions. Moreover, selective actuation of the drive members 406*a-d* in other known configurations or coordination will cause the jaws 210, 212 to open or close. Antagonistic operation of the drive members 406*a-d* advantageously reduces the number of cables required to provide full wrist 206 motion, and also helps eliminate slack in the drive members 406*a-d*, which results in more precise motion of the end effector 204.

In the illustrated embodiment, the end effector 204 is able to articulate (move) in pitch about the second or "pitch" pivot axis $P_2$, which is located near the distal end of the wrist 206. Thus, the jaws 210, 212 open and close in the direction of pitch. Moving both articulation axes $P_1$, $P_2$ closer to the therapeutic jaw surface enables minimization of the distance between the remote center of motion, therapeutic surface, and articulation axis. Having the pitch pivot axis $P_2$ as far distal as possible may be advantageous in providing a geometric advantage that helps an operator more easily get under vessels and facilitate blunt (touch) and spread dissection. This may also reduce the overall length of the end effector 204 and thereby improve surgeon access to patient anatomy during surgery by allowing discrete motion in smaller surgical spaces. This may also improve the robotic control of the instrument making user-applied motions seem more natural. This may further result in providing better reach to anatomy during dissection, such as for lymph node removal or other tissue mobilization. In other embodiments, however, the wrist 206 may alternatively be configured such that the second pivot axis $P_2$ facilitates yaw articulation of the jaws 210, 212, without departing from the scope of the disclosure.

In the illustrated embodiment, first and second electrical conductors 412*a* and 412*b* also extend longitudinally within the lumen 408, through the wrist 206, and terminate at the end effector 204 to supply electrical energy thereto. More particularly, the first electrical conductor 412*a* terminates at a first or "upper" electrode 414*a* secured to the upper jaw 210, and the second electrical conductor 412*b* terminates at a second or "lower" electrode 414*b* secured to the lower jaw 212. In some embodiments, the electrical conductors 412*a,b* may each comprise a wire, but may alternatively comprise a rigid or semi-rigid shaft, rod, or strip (ribbon) made of a conductive material. The electrical conductors 412*a,b* may be partially covered with an insulative covering (overmold) made of a non-conductive material. Routing the electrical conductors 412*a,b* to the corresponding electrodes 414*a,b*, respectively, allows the end effector 204 to operate in bipolar RF operation.

In at least one embodiment, the electrical energy conducted through the electrical conductors 412*a,b* exhibits a frequency between about 100 kHz and 1 MHz. In a process known as Joule heating (resistive or Ohmic heating) the RF energy is transformed into heat within target tissue grasped between the jaws 210, 212 due the tissue's intrinsic electrical impedance, thereby increasing the temperature of the target tissue. Heating the target tissue achieves various tissue effects such as cauterization and/or coagulation, and thus may be particularly useful for sealing blood vessels or diffusing bleeding during a surgical procedure. Heating the target tissue may also cause desiccation of the tissue, which allows the tissue to be cut (dissected) more easily.

FIG. 4B is another enlarged isometric view of the end effector 204. The upper jaw 210 (FIG. 4A) is omitted in FIG. 4B to enable viewing of various component parts of the lower jaw 212. In the illustrated embodiment, the end effector 204 comprises a combination tissue grasper and vessel sealer and includes a knife 416 (mostly occluded), alternately referred to as a "cutting element" or "blade." The knife 416 is aligned with and configured to traverse a guide track or "knife slot" 418 defined longitudinally in both the upper and lower jaws 210, 212. The knife 416 may be operatively coupled to the distal end of a drive rod 420 (alternately referred to as "knife rod," "actuation rod," or "push rod") that extends longitudinally within the lumen 408 and passes through the wrist 206. Longitudinal movement (translation) of the drive rod 420 correspondingly moves the knife 416 within the knife slot 418.

The drive rod 420 may comprise a rigid or semi rigid elongate member, such as a rod or shaft (e.g., a hypotube, a hollow rod, a solid rod, etc.), a wire, a ribbon, a push cable, or any combination thereof. The drive rod 420 can be made from a variety of materials including, but not limited to, metal (e.g., tungsten, nitinol, stainless steel, etc.), a polymer, or a composite material. The drive rod 420 may have a circular cross-section, but may alternatively exhibit a polygonal cross-section without departing from the scope of the disclosure.

Similar to the drive members 406*a-d*, the drive rod 420 may form part of the actuation systems housed within the drive housing 208 (FIG. 2). Selective actuation of a corresponding drive input will cause the drive rod 420 to move distally or proximally within the lumen 408, and correspondingly move the knife 416 in the same longitudinal direction.

In the illustrated embodiment, the knife 416 is shown received within a knife housing 422 pivotably mounted to the end effector 204. As described in more detail below, the knife housing 422 defines a central passageway through which the knife 416 and the drive rod 420 are able to extend to move the knife 416 into and along the knife slot 418. Upon firing the end effector 204, the drive rod 420 is moved (urged) distally, which correspondingly moves the knife 416 out of the knife housing 422 and into the knife slot 418. After firing is complete, the drive rod 420 is retracted proximally, which pulls the knife 416 proximally and back into the knife housing 422 until it is desired to again fire the end effector 204.

Thermally and Mechanically Symmetric Electrodes

Referring again to FIG. 4A, with continued reference to FIG. 4B, in example operation of the end effector 204, the jaws 210, 212 may be actuated to close and grasp onto tissue, following which the electrodes 414*a,b* may be supplied with electrical energy, which is transformed into heat within the grasped tissue to cauterize, coagulate, and/or otherwise seal the tissue. The knife 416 may then be advanced distally along the knife slot 418 to cut (transect) and simultaneously seal the grasped tissue. Alternatively, in other applications, the knife 416 may be advanced prior to the application of electrical energy to cut unsealed tissue to facilitate dissection of non-vascular tissue.

According to embodiments of the present disclosure, the electrodes 414*a,b* provided in the end effector 204 may be designed to be thermally and mechanically symmetric and thereby configured to optimize performance of the end effector 204 when treating and cutting tissue grasped between the jaws 210, 212. Prior vessel sealer designs commonly include only a single, isolated electrode positioned on only one of the jaws, and the opposing jaw operates as the return path on the opposite side. This design configuration results in a difference in thermal mass causing asymmetric heat signatures on opposing sides of the tissue grasped between the jaws, which may affect tissue sealing performance. In contrast, the thermally and mechanically symmetric jaws 210, 212 described herein each include a corresponding powered electrode 414*a,b*, which results in a thermally balanced thermal mass on both sides (e.g., above and below) of the grasped tissue. The presently-disclosed electrodes 414*a,b* facilitate consistent and efficient heating of the electrodes 414*a,b* and the corresponding grasped tissues due to low and equal thermal mass on both sides of the tissue.

Figure 5A:
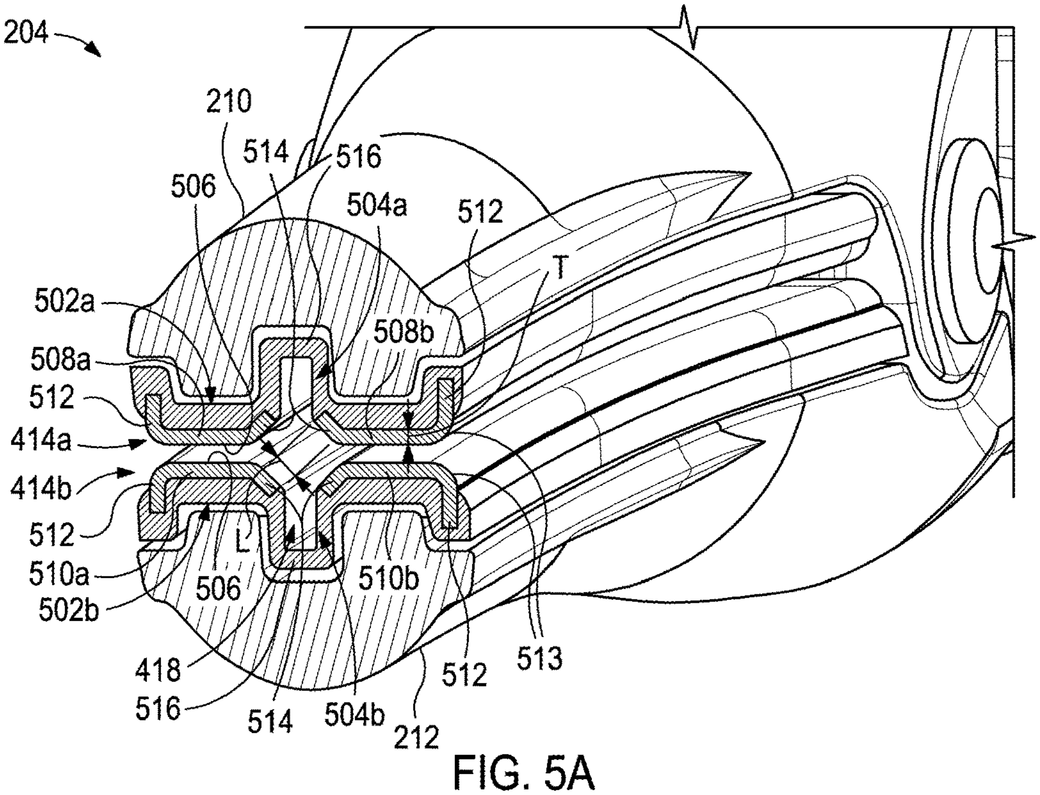
FIGS. 5A and 5B are partial cross-sectional isometric and end views, respectively, of the end effector of FIGS. 4A-4B as taken along the plane indicated in FIG. 4A, according to one or more embodiments.
Figure 5B:
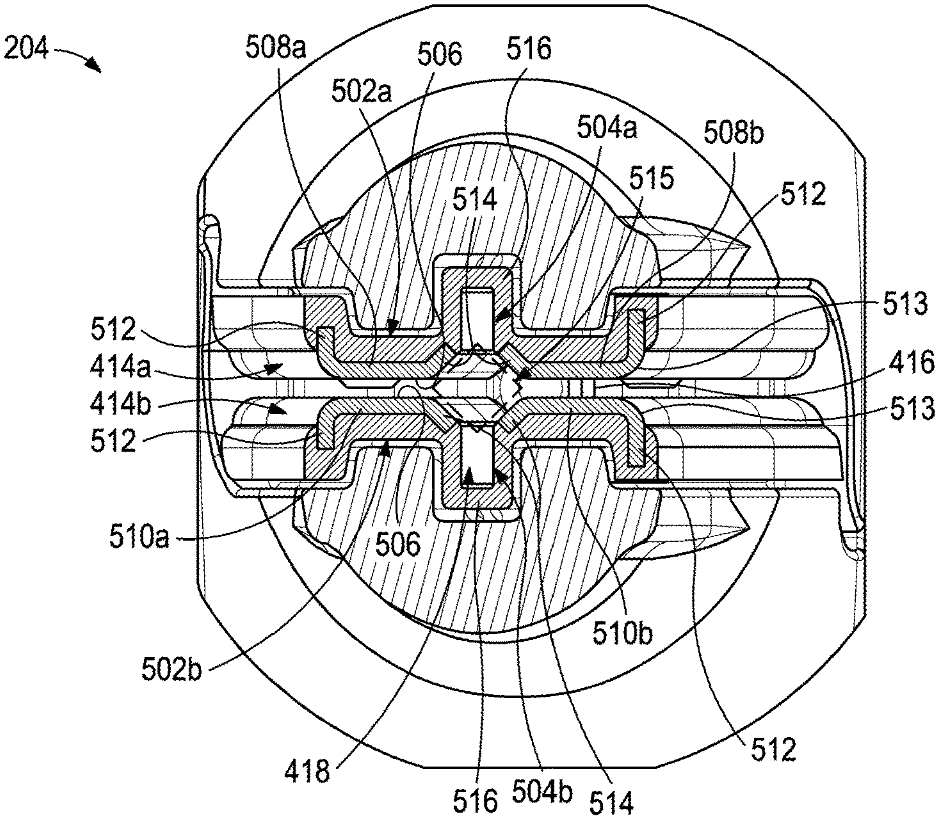

FIGS. 5A and 5B are partial cross-sectional isometric and end views, respectively, of the end effector 204, as taken along the plane indicated in FIG. 4A, according to one or more embodiments. The upper and lower jaws 210, 212 are shown in FIGS. 5A-5B in the closed position. In the closed position, the upper jaw 210 extends substantially parallel to the lower jaw 212 and the electrodes 414*a,b* interpose at least a portion of the interface between the upper and lower jaws 210, 212. Each electrode 414*a,b* is mounted to the corresponding jaw 210, 212 in conjunction with a corresponding insulator 502*a* and 502*b*, which operates to isolate the RF energy supplied to the electrodes 414*a,b* from the corresponding bodies of the jaws 210, 212 during operation.

As illustrated, the upper insulator 502*a* may be overmolded onto the upper electrode 414*a*, and the lower insulator 502*b* may be overmolded onto the lower electrode 414*b*. Each insulator 502*a,b* may comprise a non-conductive material mated or otherwise coupled to the corresponding jaw 210, 212. Suitable non-conductive materials include, but are not limited to, nylon, polyphthalamide (PPA; e.g., GRIVORY® or THERMEC™), or a combination thereof.

The electrodes 414*a,b* and the insulators 502*a,b* may cooperatively define the knife slot 418 that guides the knife 416 (FIGS. 4B and 5B) along the jaws 210, 212. More specifically, the upper insulator 502*a* and the upper electrode 414*a* may cooperatively define a first or "upper" slot portion 504*a*, and the lower insulator 502*b* and the lower electrode 414*b* may cooperatively define a second or "lower" slot portion 504*b*. When the jaws 210, 212 are closed, the upper and lower slot portions 504*a,b* are aligned such that the knife 416 extends partially into each slot portion 504*a,b* as the knife 416 traverses the knife slot 418. The slot portions 504*a,b* cooperatively direct the travel path of the knife 416 and help prevent the knife 416 from twisting or otherwise falling (leaning) to one side or the other.

The upper and lower electrodes 414*a,b* constitute mirror images of each other, and each electrode 414*a,b* provides and otherwise defines a planar sealing surface 506. When the jaws 210, 212 are closed, the planar sealing surfaces 506 are arranged substantially parallel to each other and a small gap is defined therebetween to receive (accommodate) tissue. The upper slot portion 504*a* bifurcates the planar sealing surface 506 of the upper electrode 414*a*, thereby defining left (first) and right (second) portions 508*a* and 508*b* of the upper electrode 414*a*. Similarly, the lower slot portion 504*b* bifurcates the planar sealing surface 506 of the lower electrode 414*b*, thereby defining left (first) and right (second) portions 510*a* and 510*b* of the lower electrode 414*b*.

The design and configuration of the lateral extents of the left and right portions 508*a,b* and 510*a,b* may be optimized for efficient thermal management. More specifically, the left and right portions 508*a,b* and 510*a,b* of each electrode 414*a,b* provide and otherwise define an outer lateral extent 512 extending from the corresponding planar sealing surface 506. In the illustrated embodiment, the outer lateral extent 512 (alternately referred to as the "perimeter" or "boundary") extends away from the planar sealing surface 506 and away from the opposing jaw 210, 212; e.g., out of the plane of the planar sealing surface 506 and toward the body of the corresponding jaw 210, 212. In at least one embodiment, as illustrated, the outer lateral extent 512 extends from the corresponding planar sealing surface 506 at about a 90° angle, but could alternatively extend at an angle greater or less than 90°, without departing from the scope of the disclosure.

In some embodiments, as illustrated, one or more of the outer lateral extents 512 of the electrodes 414*a,b* may be embedded within a portion of the corresponding insulator 502*a,b*. As will be appreciated, this may help retain (secure) the electrode 414*a,b* to the insulator 502*a,b* without requiring mechanical fasteners, adhesives, or an interference fit. Moreover, embedding the outer lateral extents 512 in the insulator 502*a,b* may also be advantageous in reducing the conductive pathway through tissue extending on either lateral side of the jaws 210, 212. More specifically, embedding at least a portion of the outer lateral extents 512 within the insulator 502*a,b* may result in cooler tissue protruding out each lateral side of the jaws 210, 212 as compared to end effectors with entirely exposed lateral extents.

In the illustrated embodiment, the insulator 502*a,b* extends toward but stops short of the planar sealing surface 506. As a result the electrodes 414*a,b* may provide an electrically exposed edge 513 (e.g., radius, curvature, etc.) that provides the transition between the planar sealing surface and the lateral extent 512. In other embodiments, however, and as described in more detail below, the insulator 502*a,b* may extend to and terminate at the planar sealing surface 506, thus covering and otherwise encapsulating the edge 513. In such embodiments, the heat difference in the portions of the tissue protruding out each lateral side of the jaws 210, 212 may be even cooler as compared to temperatures where the electrodes 414*a,b* directly contact the tissue during sealing.

The left and right portions 508*a,b* and 510*a,b* of each electrode 414*a,b* may further provide and otherwise define an inner lateral extent 514 extending from the corresponding planar sealing surface 506 at the knife slot 418. The inner lateral extent 514 could alternately be referred to as or characterized as an inner lateral "perimeter," "boundary," or "face". Similar to the outer lateral extents 512, each inner lateral extent 514 extends away from the planar sealing surface 506 and also away from the opposing jaw 210, 212; e.g., out of the plane of the planar sealing surface 506 and toward the body of the corresponding jaw 210, 212). In at least one embodiment, as illustrated, the inner lateral extent 514 extends away from the corresponding planar sealing surface 506 at about a 45° angle, but could alternatively extend at an angle greater or less than 45°, without departing from the scope of the disclosure.

One or more of the inner lateral extents 514 may be at least partially embedded within a portion of the corresponding insulator 502*a,b*. As will be appreciated, this may help retain (secure) the electrode 414*a,b* to the insulator 502*a,b* without the need of mechanical fasteners or an interference fit.

As forming integral parts of the corresponding upper and lower slot portions 504*a,b*, the inner lateral extents 514 help define the knife slot 418. In at least one embodiment, when the jaws 210, 212 are closed, the electrodes 414*a,b* at the inner lateral extents 514 cooperatively define a generally diamond-shaped cross-section 515 (FIG. 5B). The diamond-shaped cross-section 515 of the knife slot 418 may be sized to provide adequate space for the knife 416 (FIG. 5B) and the drive rod 420 (FIG. 4B) to extend therethrough while firing the end effector 204.

Moreover, the diamond-shape 515 of the electrodes 414*a,b* at the knife slot 418 is electrically exposed (e.g., not overmolded with the insulators 502*a,b*), which may provide a conductive pathway that creates uniform heating of tissue across the knife slot 418. This may create a thermal effect that helps desiccate tissue in the center of the knife slot 418, which makes the tissue easier to cut and ensures that the grasped tissue is fully sealed up to the cut location. Electrodes without the diamond-shaped cross-section 515 (i.e., entirely flat sealing surfaces) can fail to communicate sufficient thermal energy to the tissue at the knife slot. Having the diamond-shaped 515 knife slot 418, however, allows the thermal energy to radiate to and thereby efficiently desiccate the grasped tissue.

In some embodiments, one or both of the insulators 502*a,b* may provide or otherwise define a floor or "trough" section 516 extending laterally across the knife slot 418 and thereby structurally connecting the lateral sides of the corresponding insulators 502*a,b*. Each trough section 516 may form the bottom of the upper and lower slot portions 504*a,b*. Prior art insulators are often disconnected (separated) at the knife slot, but the insulators 502*a,b* described herein comprise monolithic components that extend across the knife slot 418 and opposing lateral sides are interconnected at the trough section 516. As will be appreciated, the trough section 516 may prove advantageous in simplifying the manufacture of the insulators 502*a,b*.

Referring specifically to FIG. 5A, the inner lateral extents 514 each provide an exposed surface area extending from the corresponding planar sealing surface 506 and toward the trough section 516, and thereby help form a portion of the knife slot 418. In some embodiments, as illustrated, the length L of one or both of the inner lateral extents 514 may be greater than a thickness T of the corresponding electrode 414*a,b*. This may prove advantageous in providing extra surface area for sealing through the knife zone.

Figure 6A:
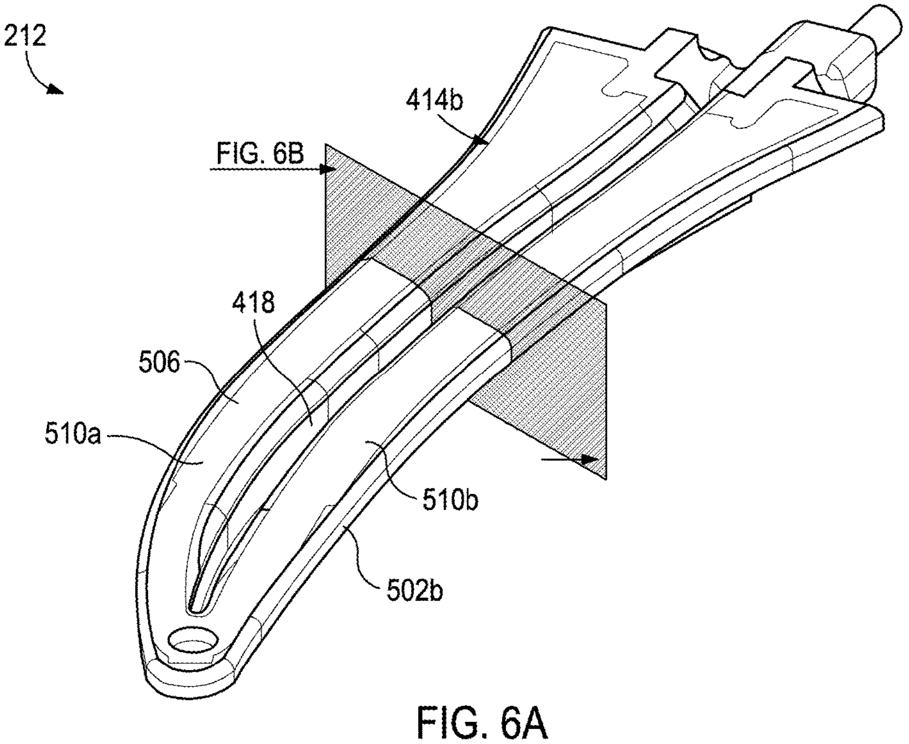
FIG. 6A is an isometric view of a portion of the lower jaw of the end effector of FIG. 2, according to one or more additional embodiments.
Figure 6B:
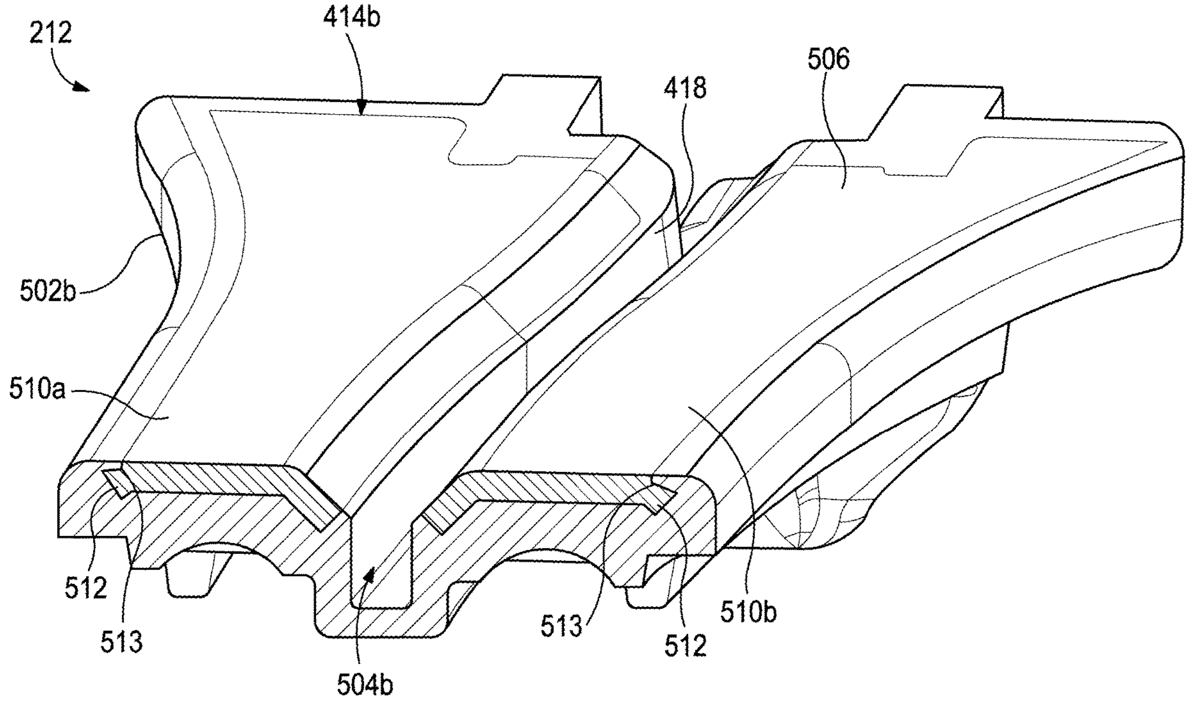
FIG. 6B is a cross-sectional view of the portion of the lower jaw of FIG. 6A, as taken along the indicated plane in FIG. 6A.

FIG. 6A is an isometric view of a portion of the lower jaw 212, according to one or more additional embodiments, and FIG. 6B is a cross-sectional view of the portion of the lower jaw 212 of FIG. 6A taken along the indicated plane in FIG. 6A. More specifically, FIGS. 6A and 6B depict the lower electrode 414*b* and the lower insulator 502*b* of the lower jaw 212. The configuration of the upper jaw 210 (FIGS. 4A and 5A-5B) may be substantially similar, thus the following discussion may be equally applicable to the upper jaw 210. The lower jaw 212 shown in FIGS. 6A-6B may be similar in some respects to the lower jaw 212 shown in FIGS. 5A-5B and therefore may be best understood with reference thereto, where like numerals will represent similar components that may not be described again in detail.

As illustrated, the lower insulator 502*b* may be overmolded onto the lower electrode 414*b*, and the lower electrode 414*b* and the lower insulator 502*b* cooperatively define the lower slot portion 504*b* of the knife slot 418. The lower slot portion 504*b* bifurcates the planar sealing surface 506 of the lower electrode 414*b*, thereby defining the left and right portions 510*a,b* of the lower electrode 414*b*.

As best seen in FIG. 6B, the outer lateral extents 512 of the lower electrode 414*b* extend away from the planar sealing surface 506 and toward the body of the lower jaw 212 at about a 45° angle, but could alternatively extend at an angle greater or less than 45°, without departing from the scope of the disclosure. The outer lateral extents 512 may also be embedded within the lower insulator 502*b*, which encapsulates the lateral extents 512 by extending to and terminating at the planar sealing surface 506. As a result, the lower insulator 502*b* may provide a generally flush interface and finish with the planar sealing surface 506. In the embodiment shown in FIGS. 5A-5B, the lower insulator 502*b* stops short of the planar sealing surface 506, which leaves the edge 513 (radius, corner, etc.) of the lower electrode 414*b* exposed. In the illustrated embodiment, however, the edge 513 of the lower electrode 414*b* is covered by the lower insulator 502*b*, which finishes flush with the planar sealing surface 506.

Figure 7A:
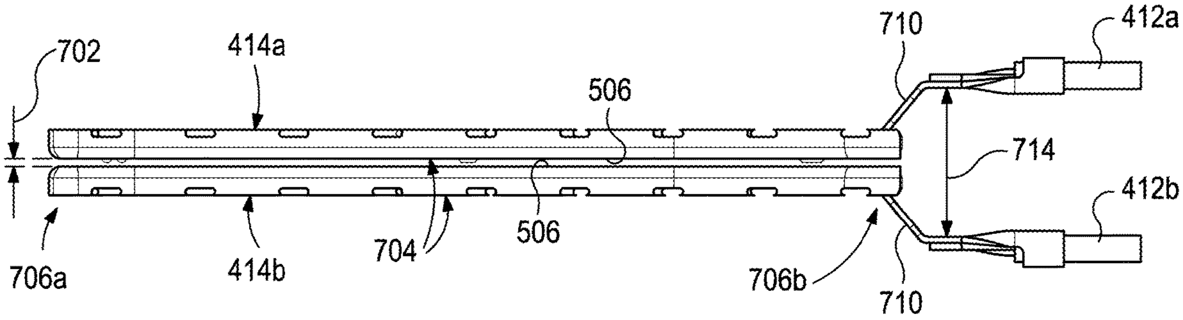
FIGS. 7A and 7B are side and isometric views, respectively, of the upper and lower electrodes, according to one or more embodiments.
Figure 7B:
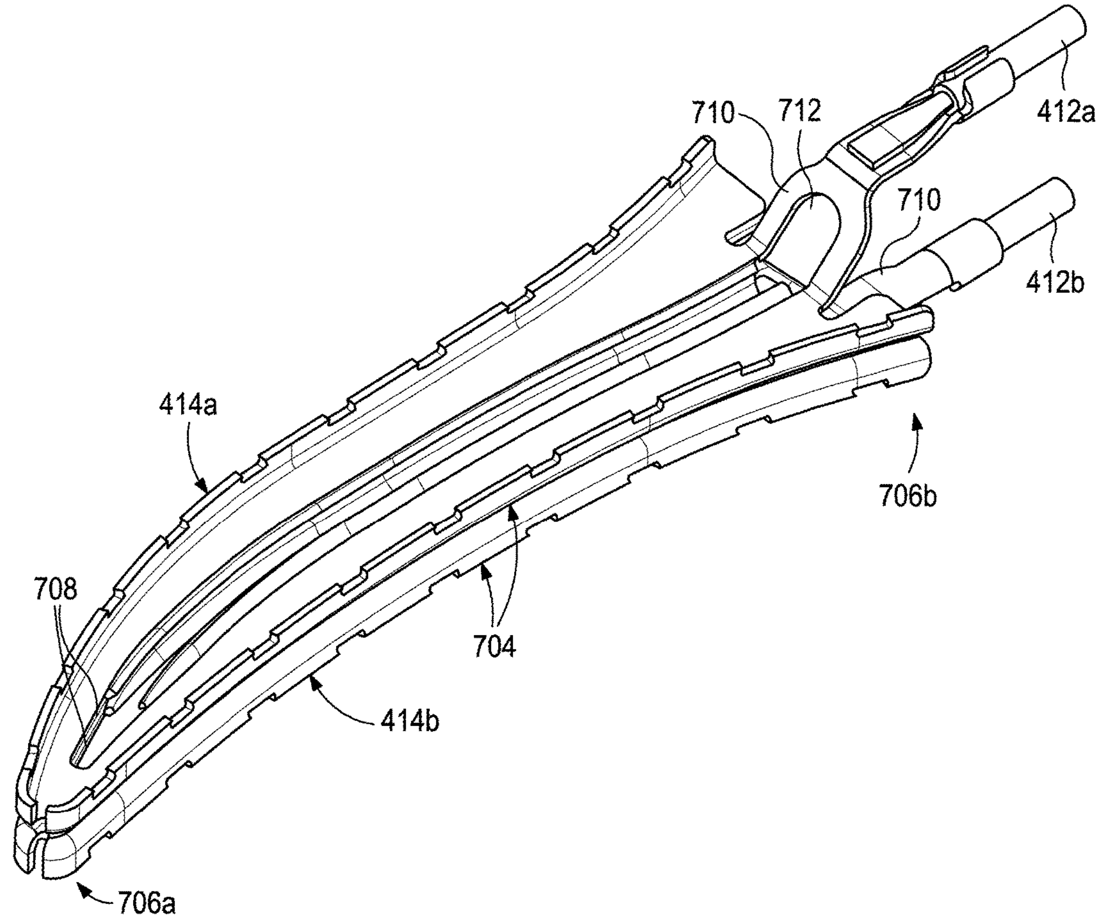

FIGS. 7A and 7B are side and isometric views, respectively, of the upper and lower electrodes 414*a,b*, according to one or more embodiments. As indicated above, the upper and lower electrodes 414*a,b* may constitute mirror images of each other. In FIGS. 7A and 7B, the electrodes 414*a,b* are depicted in a configuration when the jaws 210, 212 (FIGS. 2, 4A, 5A-5B) are in the closed position. In the closed position, the electrodes 414*a,b* are arranged substantially parallel to each other and a small gap 702 (FIG. 7A) is defined therebetween to receive (accommodate) tissue.

As illustrated, each electrode 414*a,b* includes an elongate body 704 having a first or "distal" end 706*a* and a second or "proximal" end 706*b* opposite the distal end 706*a*. The body 704 may be made of a variety of rigid, conductive materials, such as a metal. Example conductive materials include, but are not limited to, stainless steel, aluminum, silver, copper, and alloys thereof. Alternatively, stainless steel could also be used as a substrate over which gold, silver, or platinum could be applied through a plating process. An elongate channel 708 (FIG. 7B) is defined in the body 704 of each electrode 414*a,b* and extends between the distal and proximal ends 706*a,b*. The elongate channel 708 helps define the knife slot 418 (FIGS. 5A-5B) in the upper and lower jaws 210, 212 (FIGS. 2, 4A, 5A-5B). As best seen in FIG. 7B, the elongate channels 708 substantially align when the jaws 210, 212 are closed.

Each electrode 414*a,b* may provide an electrical connector 710 positioned at and otherwise extending from the proximal end 706*b*. The electrical connector 710 provides a location where the first and second electrical conductors 412*a,b* can be placed in electrical communication with the electrodes 414*a,b*, respectively. More specifically, the first electrical conductor 412*a* terminates at and is electrically coupled to the electrical connector 710 of the upper electrode 414*a*, and the second electrical conductor 412*b* terminates at and is electrically coupled to the electrical connector 710 of the lower electrode 414*b*. In contrast to vessel sealers that incorporate a single electrical conductor and relies on a mechanical metallic drive train for the conductive return pathway on an opposing jaw, the presently-described electrical conductors 412*a,b* are routed directly to the corresponding electrodes 414*a,b*. While the upper and lower electrodes 414*a,b* may be mirror images of each other, each electrode 414*a,b* exhibits a different polarity. As will be appreciated, this direct routing and electrical communication minimizes electrical losses, which enables better signal integrity for driving system response and ensures more controlled impedance values that improve the ability to do distal sensing of tissue properties, and better detection of seal progression.

In some embodiments, the electrical connectors 710 may form an integral part of the corresponding electrode 414*a,b* from which it extends. In such embodiments, each electrode 414*a,b* and corresponding electrical connector 710 may comprise a stamped, metal part, which may prove advantageous in simplifying the manufacturing process of the electrodes 414*a,b*.

Moreover, in at least one embodiment, as illustrated, the elongate channel 708 defined in each electrode 414*a,b* may extend into the electrical connector 710, which forms or otherwise defines a generally U-shaped passage 712 (FIG. 7B). Consequently, the electrodes 414*a,b* may be bridged (connected) at both ends 706*a,b*, which allows for centered, embedded connection of the electrical conductors 412*a,b* for both electrodes 414*a,b*.

As best seen in FIG. 7A, the electrical connectors 710 may extend away from the corresponding electrodes 414*a,b* and, more particularly, away from the plane of the corresponding planar sealing surface 506. In such embodiments, the electrical connectors 710 may extend at about a 45° angle, but could alternatively extend at an angle greater or less than 45°, without departing from the scope of the disclosure. The electrical connectors 710 may extend below the corresponding planar sealing surface 506 such that a gap 714 (FIG. 7A) is defined between the electrical connectors 710. The gap 714 may prove advantageous in providing space to accommodate the knife 416 (FIGS. 4B and 5B) and the knife housing 422 (FIG. 4B). Moreover, the knife 416 may be able to pass through the U-shaped passage 712 provided by each electrical connector 710 as it traverses the knife slot 418 operation.

Improved Jaw Mechanism

Figure 8A:
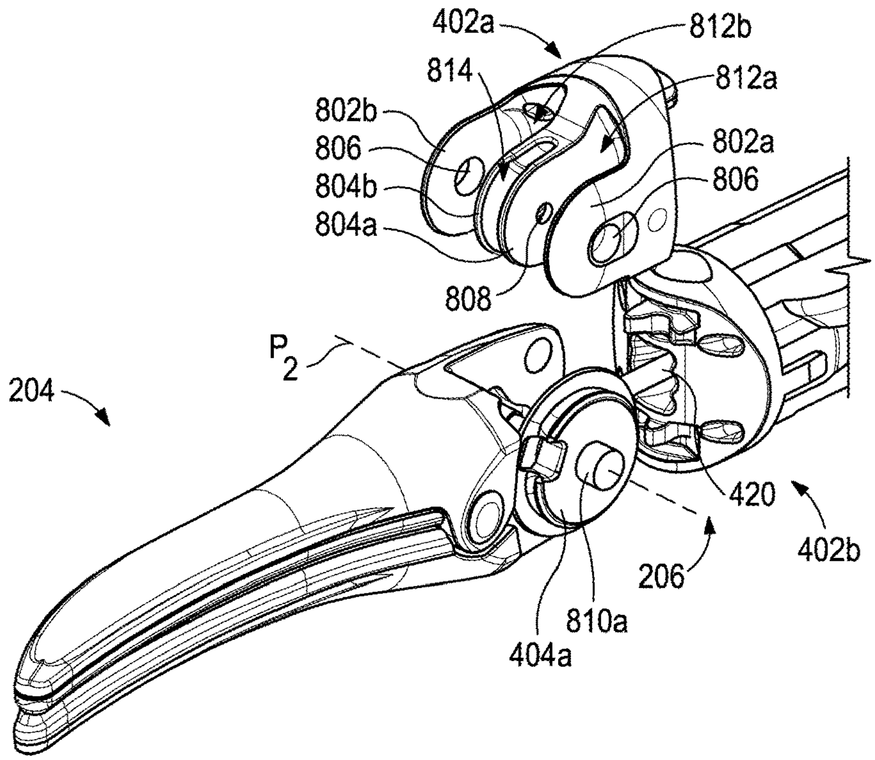
FIGS. 8A and 8B are an isometric, partially exploded views of the end effector and the wrist of FIGS. 2 and 4A-4B, as taken from right and left vantage points, respectively.
Figure 8B:
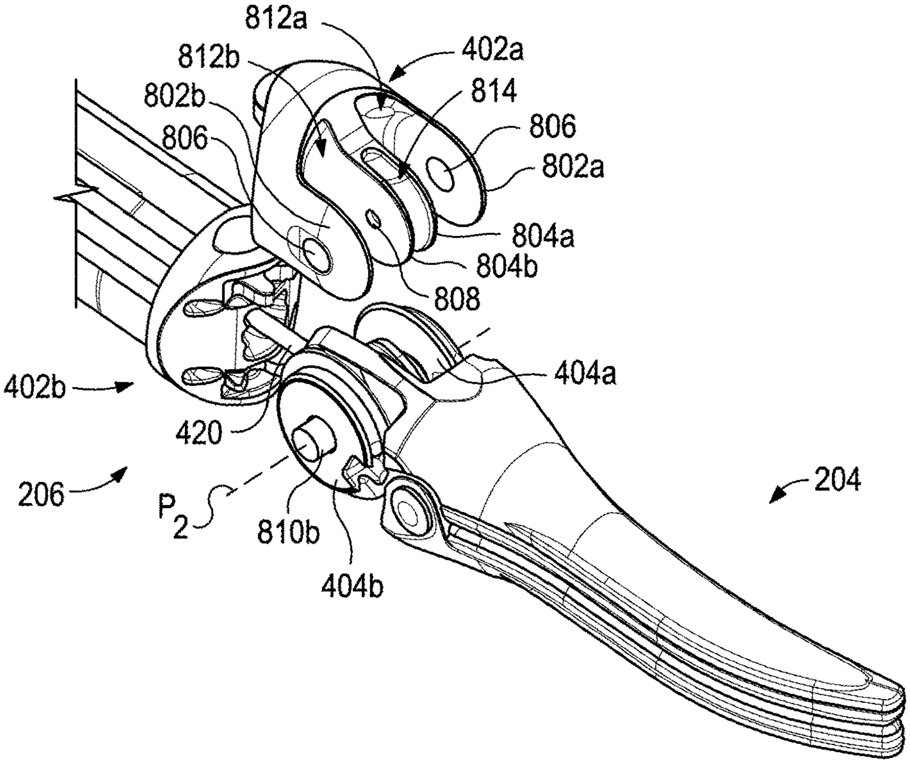

FIGS. 8A and 8B are isometric, partially exploded views of the end effector 204 and the wrist 206 of FIGS. 2 and 4A-4B, as taken from right and left vantage points, respectively. In FIGS. 8A-8B, the distal clevis 402*a* is shown exploded vertically from the remaining portions of the wrist 206, thus exposing various internal parts of the wrist 206. The drive members 406*a-d* (FIG. 4A) and the electrical conductors 412*a,b* (FIGS. 4A-4B) are omitted from FIGS. 8A-8B to enable better viewing of the component parts of the wrist 206.

In the illustrated embodiment, the distal clevis 402*a* is depicted as a monolithic, one-piece structure, but could alternatively be made of two or more component parts, without departing from the scope of the disclosure. As discussed in more detail below, the proximal end of the distal clevis 402*a* may be rotatably mounted to the distal end of the proximal clevis 402*b*, and vice versa, which allows the wrist 206 to articulate in "yaw" about the first pivot axis $P_1$ (FIG. 4A).

The distal clevis 402*a* provides and otherwise defines a pair of outer lobes 802*a* and 802*b* and a pair of inner lobes 804*a* and 804*b*. The outer and inner lobes 802*a,b* and 804*a,b* each extend distally, and the inner lobes 804*a,b* interpose the outer lobes 802*a,b*. Each outer lobe 802*a,b* defines an axle aperture 806, and each inner lobe 804*a,b* defines a pin aperture 808. The axle and pin apertures 806, 808 are co-axially aligned along the second pivot axis $P_2$ of the wrist 206 and configured to support first and second axles 810*a* (FIG. 8A) and 810*b* (FIG. 8B). More specifically, an outer end of the first axle 810*a* may be configured to be received within the axle aperture 806 of the first outer lobe 802*a*, and an inner end of the first axle 810*a* may be configured to be received within the pin aperture 808 of the first inner lobe 804*a*. Similarly, an outer end of the second axle 810*b* may be configured to be received within the axle aperture 806 of the second outer lobe 802*b*, and an inner end of the second axle 810*b* may be configured to be received within the pin aperture 808 of the second inner lobe 804*b*.

The first and second pulleys 404*a,b* may be rotatably mounted to the distal clevis 402*a* at the first and second axles 810*a,b*, thereby being able to rotate about the second pivot axis $P_2$. More specifically, the first pulley 404*a* may be received within a gap 812*a* defined between the first outer and inner lobes 802*a*, 804*a* and rotatably mounted to the first axle 810*a*, and the second pulley 404*b* may be received within a gap 812*b* defined between the second outer and inner lobes 802*b*, 804*b* and configured to be rotatably mounted to the second axle 810*b*.

In some embodiments, the first and second axles 810*a,b* may be secured (e.g., welded) to one or both of the axle and pin apertures 806, 808. In such embodiments, the pulleys 404*a,b* may be rotatably mounted to the first and second axles 810*a,b*, respectively, such that they are free to rotate. In other embodiments, however, the pulleys 404*a,b* may be secured (e.g., welded) to the first and second axles 810*a,b*. In such embodiments, the first and second axles 810*a,b* may be freely rotatable within the corresponding axle and pin apertures 806, 808. In yet other embodiments, the first and second axles 810*a,b* may be freely rotatable and not secured to any other component of the wrist 206, without departing from the scope of the disclosure.

As illustrated, a central gap 814 may be defined between the inner lobes 804*a,b*. The central gap 814 may be configured to accommodate the drive rod 420 and the electrical conductors 412*a,b* (FIGS. 4A-4B) as extending to the end effector 204.

Figure 9A:
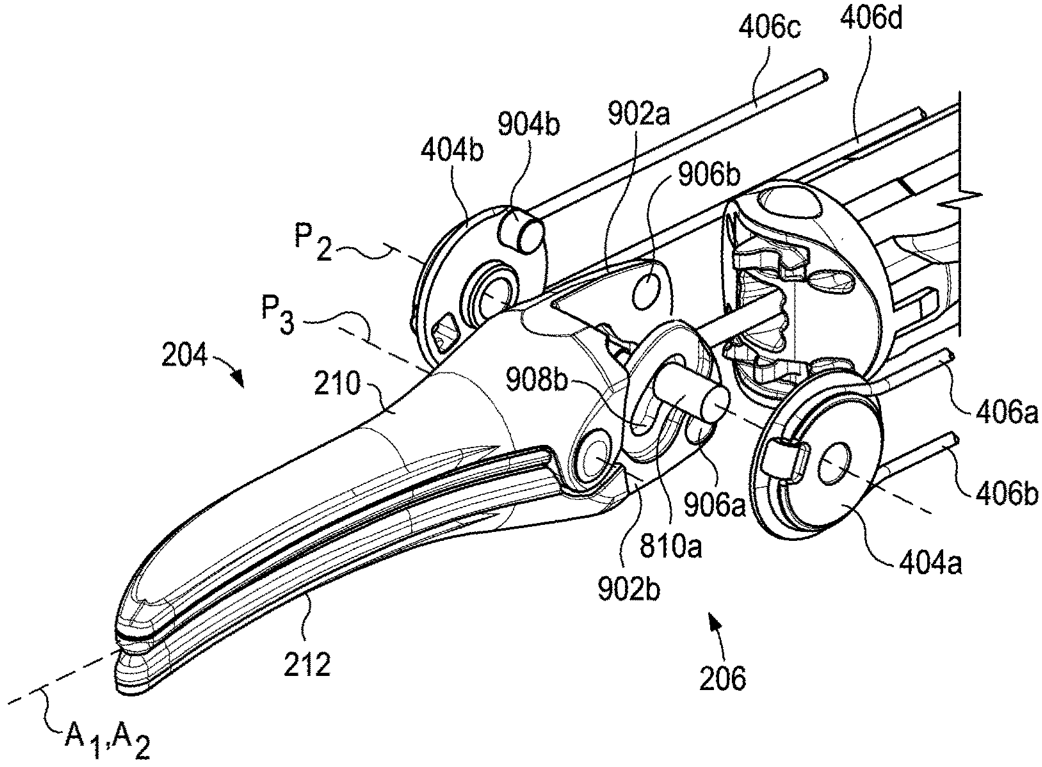
FIGS. 9A and 9B are additional isometric, exploded views of the end effector and the wrist of FIGS. 2 and 4A-4B from right and left vantage points, respectively.
Figure 9B:
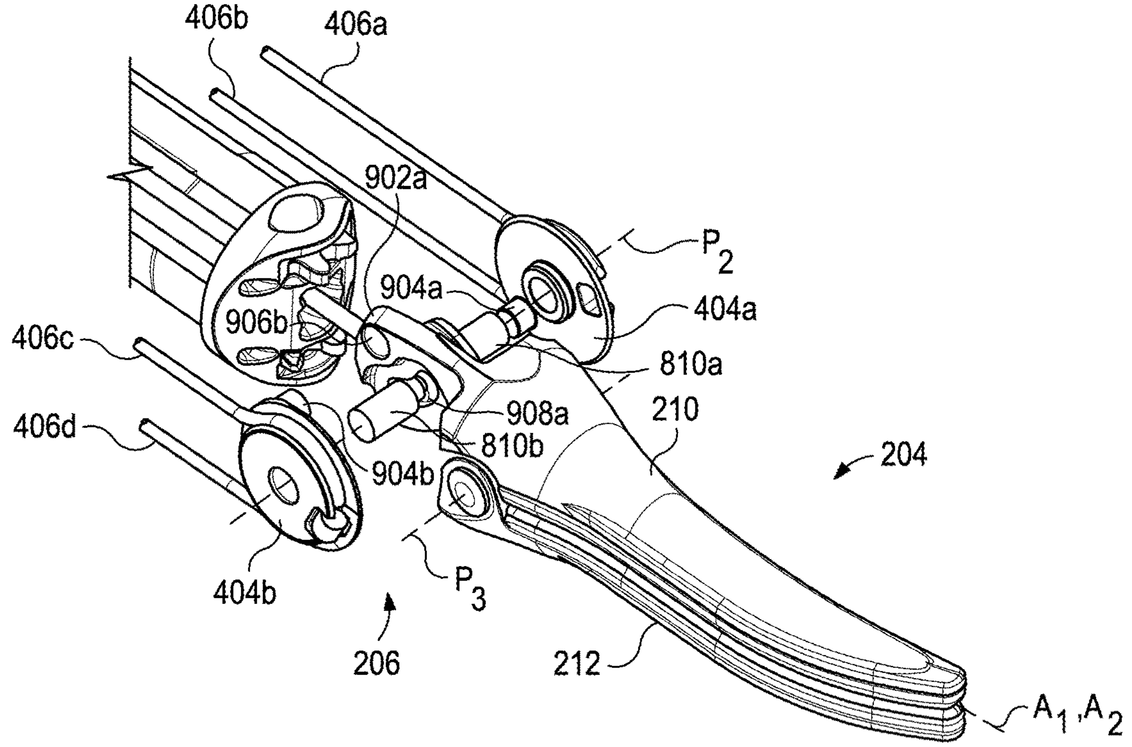

FIGS. 9A and 9B are additional isometric, exploded views of the end effector 204 and the wrist 206 from right and left vantage points, respectively. In FIGS. 9A-9B, the distal clevis 402*a* (FIGS. 8A-8B) is omitted for simplicity, and the first and second pulleys 404*a,b* and the drive members 406*a-d* are shown exploded laterally from the remaining portions of the end effector 204 and the wrist 206. As illustrated, the jaws 210, 212 may be pivotably and rotatably coupled to each other at a third pivot axis $P_3$, alternately referred to as a "jaw pivot axis". The third pivot axis $P_3$ may be parallel to the second pivot axis $P_2$ and orthogonal to the first pivot axis $P_1$ (FIG. 4A). In at least one embodiment, the longitudinal axes $A_1$, $A_2$ of the shaft 202 (FIG. 2) and the end effector 204, respectively, are perpendicular to and intersect the third pivot axis $P_3$. In some embodiments, as illustrated, both jaws 210, 212 may be configured to simultaneously move and pivot about the jaw pivot axis $P_3$ to pivot the jaws 210, 212 between the open and closed positions, and may thus be referred to as "bifurcating" jaws. In other embodiments, however, one of the jaws 210, 212 may be configured to pivot or rotate while the other jaw 210, 212 remains stationary, without departing from the scope of the disclosure.

Figure 10A:
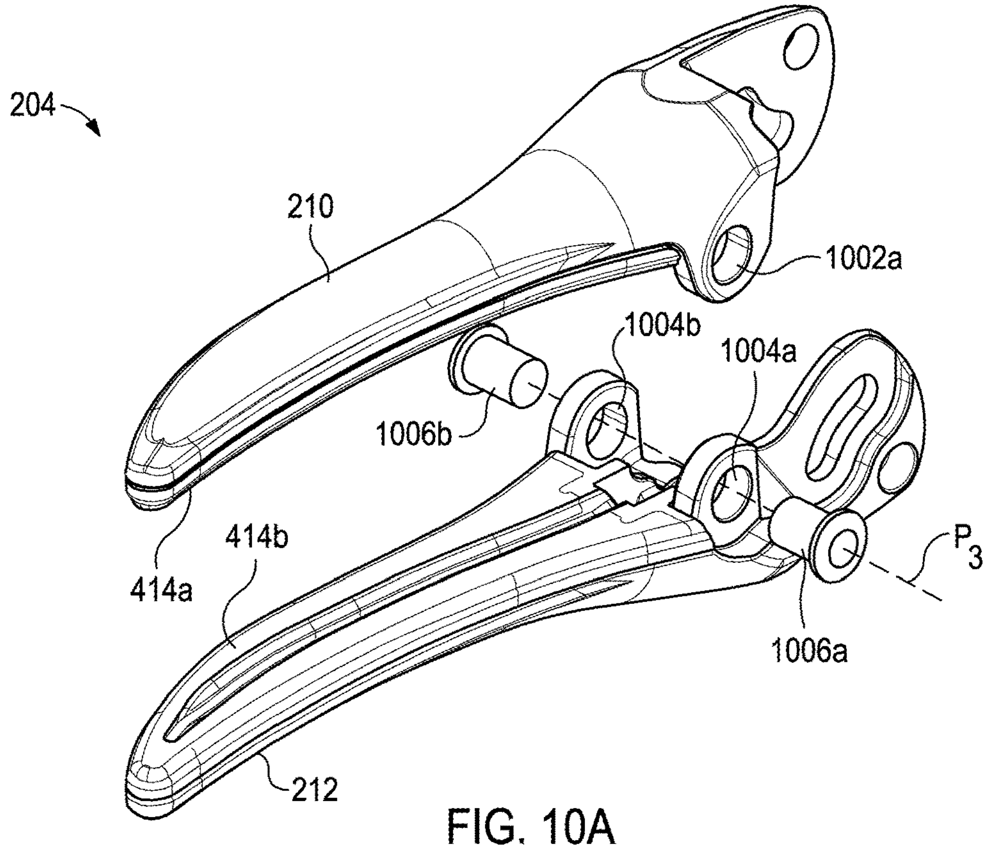
FIGS. 10A and 10B, illustrated are isometric exploded views of the end effector from left and right vantage points, respectively, according to one or more embodiments.
Figure 10B:
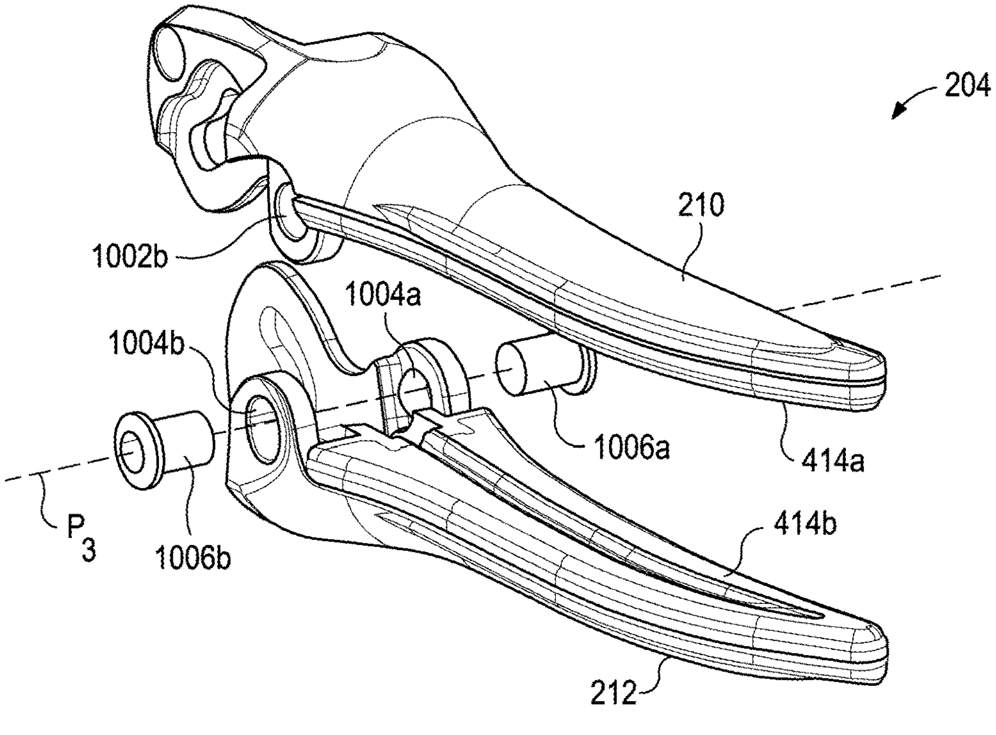

Referring briefly to FIGS. 10A and 10B, illustrated are isometric exploded views of the end effector 204 from left and right vantage points, respectively, according to one or more embodiments. In FIGS. 10A-10B, the upper and lower jaws 210, 212 are shown exploded vertically from each other. As illustrated, the upper jaw 210 provides and otherwise defines first and second jaw axle apertures 1002*a* and 1002*b* (FIG. 10B) located at or near the proximal end of the upper jaw 210. Similarly, the lower jaw 212 includes first and second jaw axle apertures 1004*a* and 1004*b* located at or near the proximal end of the lower jaw 212.

The jaw axle apertures 1002*a,b* of the upper jaw 210 are coaxially aligned, and the jaw axle apertures 1004*a,b* of the lower jaw 212 are also coaxially aligned. When the end effector 204 is properly assembled, the jaw axle apertures 1002*a,b* of the upper jaw 210 will be aligned coaxially with the jaw axle apertures 1004*a,b* of the lower jaw 212. More particularly, when the end effector 204 is assembled, the first jaw axle apertures 1002*a*, 1004*a* will be juxtaposed against each other, and the second jaw axle apertures 1002*b*, 1004*b* will be juxtaposed against each other such that all jaw axle apertures 1002*a,b* and 1004*a,b* will be axially aligned along the third pivot axis $P_3$.

The jaws 210, 212 may be pivotably coupled along the third pivot axis $P_3$ using one or more jaw axles, shown as a first jaw axle 1006*a* and a second jaw axle 1006*b*. The first jaw axle 1006*a* may be configured to be received within the axially aligned first jaw axle apertures 1002*a*, 1004*a*, and the second jaw axle 1006*b* may be configured to be received within the axially aligned second jaw axle apertures 1002*b*, 1004*b*. Once the first and second jaw axles 1006*a,b* are properly installed, the jaws 210, 212 will be pivotable about the third pivot axis $P_3$ between the open and closed positions.

Having the jaws 210, 212 rotatably (pivotably) coupled together at the third pivot axis $P_3$ may prove advantageous for a variety of reasons. First, this can ensure that the center plane, the sealing surfaces (e.g., the planar sealing surfaces 506 of FIGS. 5A-5B), and yaw position of the jaws 210, 212 all remain centered and controlled between the two drive pulleys; e.g., the pulleys 404*a,b* of FIGS. 8A-8B and 9A-9B. Second, this also reduces components and assembly complexity of the end effector 204, which can result in significant cost savings. Reduction in components will also help to reduce the tolerance stack-ups on jaw gap, which is critical for sealing. And third, this can reduce interfaces for positioning the yaw plane of the end effector 204, thus lowering backlash and reducing sliding friction in closure and yaw motions of the jaws 210, 212.

Moreover, as mentioned above, the longitudinal axes $A_1$, $A_2$ (FIGS. 9A-9B) of the shaft 202 (FIG. 2) and the end effector 204, respectively, may perpendicularly intersect (cross through) the third pivot axis $P_3$. Consequently, the sealing plane of the end effector 204 (e.g., the plane formed by the planar sealing surfaces 506 of FIGS. 5A-5B) may be centered relative to the end effector 204 and the shaft 202 to balance the symmetric jaws 210, 212 that both carry an electrode 414*a,b*. Having the sealing plane of the end effector 204 at the centerline of the device also allows for equal stiffness of the jaws 210, 212, and thus equal deflection of the jaws 210, 212 under loading.

Referring again to FIGS. 9A-9B, the upper jaw 210 provides a first jaw extension 902*a* and the lower jaw 212 provides a second jaw extension 902*b* (FIG. 9A), and each jaw extension 902*a,b* extends proximally from the corresponding jaws 210, 212. The second pulley 404*b* may be rotatably coupled (e.g., pinned) to the first jaw extension 902*a* such that movement (rotation) of the second pulley 404*b* correspondingly pivots the upper jaw 210 about the third pivot axis $P_3$. Similarly, the first pulley 404*a* may be rotatably coupled (e.g. pinned) to the second jaw extension 902*b* such that movement (rotation) of the first pulley 404*a* correspondingly pivots the lower jaw 212 about the third pivot axis $P_3$.

More particularly, in the illustrated embodiment, the first pulley 404*a* may provide or define a first drive pin 904*a* (FIG. 9B) configured to mate with a first jaw aperture 906*a* (FIG. 9A) defined on the second jaw extension 902*b*, and the second pulley 404*b* may provide or define a second drive pin 904*b* configured to mate with a second jaw aperture 906*b* defined on the first jaw extension 902*a*. The first and second drive pins 904*a,b* are eccentric to the second pivot axis $P_2$ when the pulleys 404*a,b* are mounted to the jaw axles 810*a,b*. Consequently, mating the first and second drive pins 904*a,b* with the second and first jaw apertures 906*b,a*, respectively, allows the pulleys 404*a,b* to rotate about the second pivot axis $P_2$ and simultaneously pivot the jaws 210, 212 about the third pivot axis $P_3$ and between the open and closed positions.

In an alternative embodiment, the first and second drive pins 904*a,b* may be provided on the first and second jaw extensions 902*a,b*, and the first and second jaw apertures 906*a,b* may be provided on the pulleys 404*a,b*, or any combination thereof. Moreover, the jaw apertures 906*a,b* need not be through-holes, as depicted, but could alternatively comprise recesses defined in the jaw extensions 902*a,b* (or the pulleys 404*a,b*) and sized and otherwise configured to receive the drive pins 904*a,b*.

Selective actuation and antagonistic operation of the drive members 406*a-d* can open or close the jaws 210, 212. More specifically, because the jaws 210, 212 are eccentrically pinned to the pulleys 404*a,b*, as generally described above, selectively actuating the drive members 406*a-d* such that the pulleys 404*a,b* rotate in opposite angular directions may result in the jaws 210, 212 opening or closing about the third pivot axis $P_3$. Selective actuation and antagonistic operation of the drive members 406*a-d* may also cause the end effector 204 to articulate at the wrist 206 in both pitch and yaw directions. More particularly, selectively actuating the drive members 406*a-d* such that the pulleys 404*a,b* rotate in the same angular direction may result in the jaws 210, 212 pivoting about the second pivot axis $P_2$ and thereby moving the end effector 204 up or down in pitch. Moreover, selective actuation of a first connected pair of drive members 406*a-d* while relaxing a second pair of connected drive members 406*a-d* may cause the end effector 204 to pivot about the first pivot axis $P_1$ (FIG. 4A) and thereby move in yaw (left or right). The drive pins 904*a,b* may be optimized to deliver consistent tension in the drive members 406*a-d* at clamping loads, while maximizing movement.

Still referring to FIGS. 9A-9B, the first jaw extension 902*a* may further define a first arcuate slot 908*a* (FIG. 9B), and the second jaw extension 902*b* may similarly define a second arcuate slot 908*b* (FIG. 9A). The first axle 810*a* may be configured to extend through the second arcuate slot 908*b*, and the second axle 810*b* may be configured to extend through the first arcuate slot 908*a*. As the jaws 210, 212 pivot between the closed and open positions, the axles 810*a,b* traverse the corresponding arcuate slots 908*a,b*.

In some embodiments, the arcuate slots 908*a,b* may be used to help prevent over-rotation of the jaws 210, 212 during operation. More specifically, each end of the arcuate slots 908*a,b* provides and otherwise defines a mechanical hard stop. As the jaws 210, 212 move to the open position, the axles 810*a,b* will traverse the corresponding arcuate slots 908*a,b* and may eventually engage the mechanical hard stop at an end of the arcuate slot 908*a,b*. Engaging the hard stop will prevent the jaws 210, 212 from pivoting further in the open direction, which could result in over-rotation and inadvertently achieving a controls singularity, which could lock the jaws 210, 212. If the drive pins 904*a,b* are over-rotated to a point that they rotate past (cross over) the longitudinal axis $A_1$ of the shaft or the longitudinal axis $A_2$ of the end effector 204 or otherwise become co-axially aligned, this could result in controls singularity, which creates unstable yaw positioning. Reaching controls singularity theoretically provides the jaws 210, 212 with the ability to rotate about different axes, thus eliminating finite control of yaw.

In other embodiments, however, the robotic controllers of the surgical tool 200 (FIG. 2) may be programmed and otherwise configured to prevent over-rotation of the jaws 210, 212 via selective actuation of the drive members 406*a,b*. In such embodiments, the mechanical hard stops of the arcuate slots 908*a,b* may serve as a fail-safe mechanism that prevents over-rotation in the event the robotic controllers or programming malfunction.

Figure 11A:
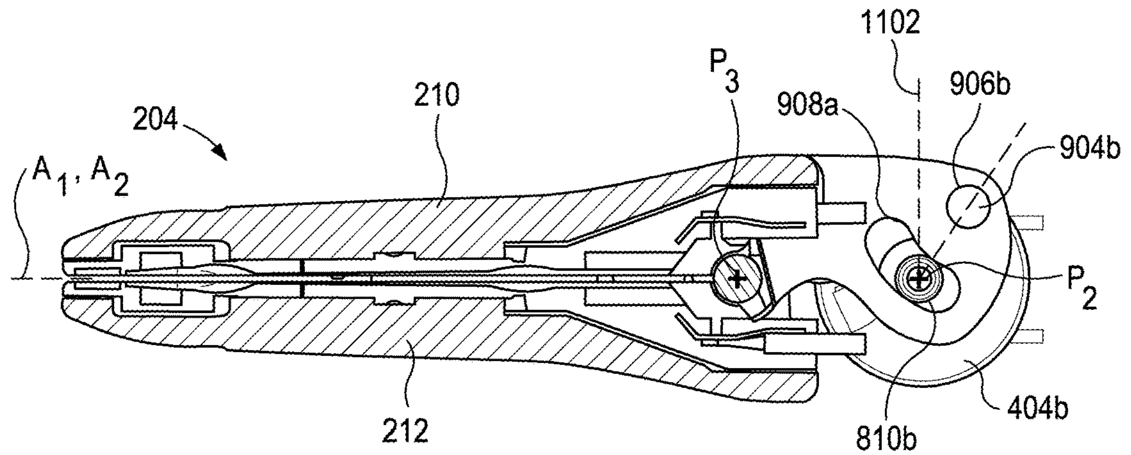
FIGS. 11A-11B are cross-sectional side views of the end effector in the closed and open positions, respectively, according to one or more embodiments.
Figure 11B:
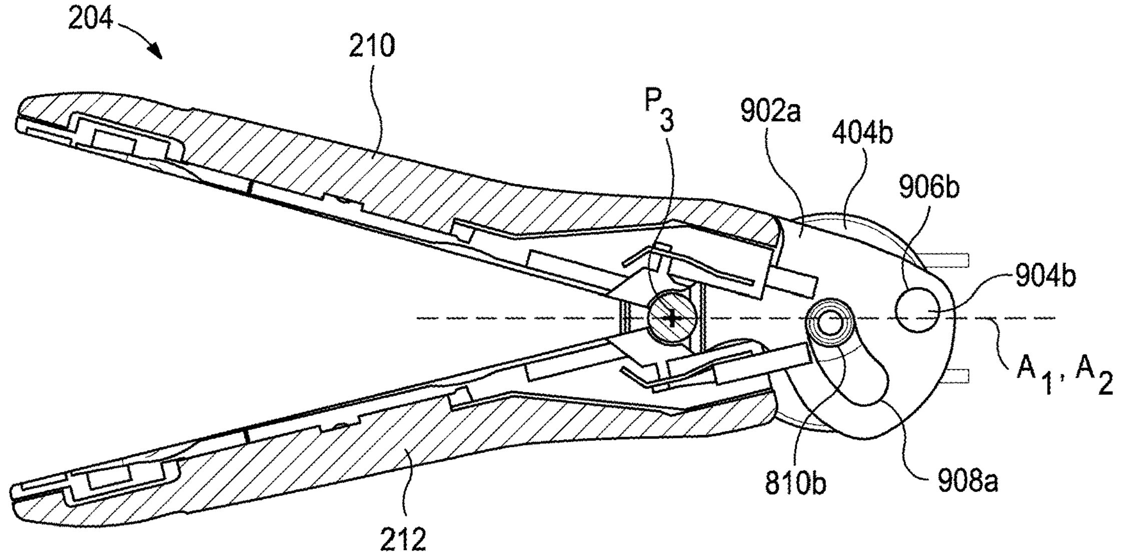

FIGS. 11A-11B are cross-sectional side views of the end effector 204 in the closed and open positions, respectively, according to one or more embodiments. In FIGS. 11A-11B, the second pulley 404*b* is shown pinned to the first jaw extension 902*a* of the upper jaw 210, but the following discussion is equally applicable to the first pulley 404*a* (FIGS. 9A-9B) being pinned to the second jaw extension 902*b* (FIGS. 9A-9B) of the lower jaw 212. As described above, the second drive pin 904*b* of the second pulley 404*b* is configured to mate with the second jaw aperture 906*b* defined on the first jaw extension 902*a* such that movement (rotation) of the second pulley 404*b* correspondingly pivots the upper jaw 210 about the third pivot axis $P_3$. Moreover, the second axle 810*b* extends through and traverses the first arcuate slot 908*a* of the first jaw extension 902*a* as the jaws 210, 212 pivot between the closed and open positions.

With reference to FIG. 11A, the end effector 204 may be operated in such a manner so as to prevent the second drive pin 904*b* from rotating "over-center" when approaching or reaching the fully closed position. More particularly, the controls system operating the end effector 204 or the configuration of the first arcuate slot 908*a* may be configured to prevent the second driver pin 904*b* from reaching or rotating past a centerline 1102 of the second pulley 404*b*, where the centerline 1102 is a plane passing through the second pivot axis $P_2$ and perpendicular to the longitudinal axis $A_1$ of the shaft 202 (FIG. 2) or the longitudinal axis $A_2$ of the end effector 204. Approaching the "over-center" condition at the closed position, while not surpassing it, ensures low tension in the drive members 406*a-d* (FIGS. 9A-9B), while balancing the motion of the drive pin 904*b* such that jaws 210, 212 do not inadvertently lock in the closed position and instead remain reactive to user input requests for jaw motion. If the second drive pin 904*b* were somehow able to rotate over-center and past the centerline 1102, the jaws 210, 212 could lock and would require a large amount of force to return from the over-center condition.

In FIG. 11B, the end effector 204 may be operated in such a manner so as to prevent the second drive pin 904*b* from rotating past (crossing over) a plane extending through the longitudinal axes $A_1$, $A_2$, which could result in controls singularity. More particularly, the controls system operating the end effector 204 or the configuration of the first arcuate slot 908*a* may be configured to prevent the second driver pin 904*b* from over-rotating past the longitudinal axes $A_1$, $A_2$, which could also result in the second drive pin 904*b* becoming concentrically aligned with the first drive pin 904*a* (FIGS. 9A-9B) and thereby achieving controls singularity that could lock up the end effector 204 and create unstable yaw positioning.

Figure 11C:
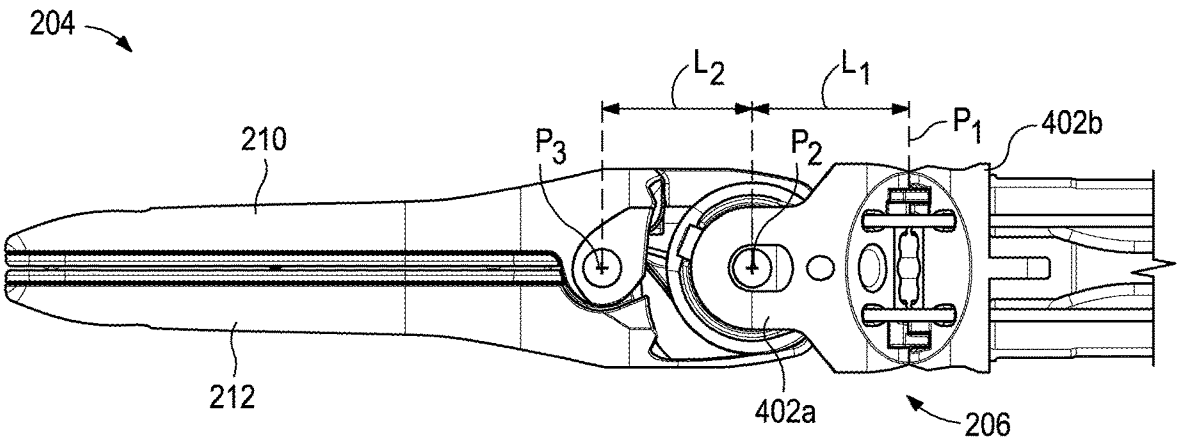
FIG. 11C is a schematic side view of the end effector and the wrist, according to one or more embodiments.

FIG. 11C is a schematic side view of the end effector 204 and the wrist 206, according to one or more embodiments. As illustrated, and as discussed above, the distal and proximal clevises 402*a,b* may be rotatably mounted to each other at the first pivot axis $P_1$ of the wrist 206, which provide "yaw" articulation of the wrist 206, and the jaws 210, 212 are rotatably mounted to the distal clevis 402*a* at the second or pivot axis $P_2$, which provides "pitch" articulation of the wrist 206. Moreover, the jaws 210, 212 are pivotably coupled to each other at the third pivot axis $P_3$, alternately referred to as a "jaw pivot axis".

The first and second pivot axes $P_1$, $P_2$ are separated from each other by a first axial length $L_1$, and the jaw pivot axis $P_3$ is separated from the second pivot axis $P_2$ by a second axial length $L_2$. According to embodiments of the present disclosure, the second axial length $L_2$ may be equal to or smaller (shorter) than the first axial length $L_1$. In combination with reduced compliments and simplified linkage of the jaws 210, 210 directly to each other, allows for a shorter mechanism that provides better access and dissection in the articulated postures. Accordingly, having a second axial length $L_2$ equal to or shorter than the first axial length $L_1$, may prove advantageous in providing easier access into tight anatomy.

Moreover, in combination with the knife 416 (FIGS. 4B and 5B) and its corresponding knife housing 422 (FIG. 4B) being centrally located within the end effector 204, having the second axial length $L_2$ equal to or shorter than the first axial length $L_1$ is an improvement over prior or conventional end effectors. As will be described in greater detail below, the unique architecture and internal structure of the end effector 204 and the distal clevis 402*a*, and how they are operatively coupled, allows for an open central area that accommodates the knife 416 and the knife housing 422. In contrast, prior end effectors have architecture and internal structure that occludes or extends across any central area, thus eliminating the potential to include a centrally-located knife and knife housing. Attempts to include the knife and knife housing would necessarily result in the second axial length $L_2$ being longer than the first axial length $L_1$.

Referring again to FIGS. 9A-9B, with continued reference to FIGS. 11A-11B, in some embodiments the end effector 204 may be designed such that the pulleys 404*a,b* need only rotate between the centerline 1102 and the longitudinal axes $A_1$, $A_2$ (e.g., less than) 90° to obtain about 80-100 Newtons of clamping force.

Dual Gear Snake Wrist

Figure 12A:
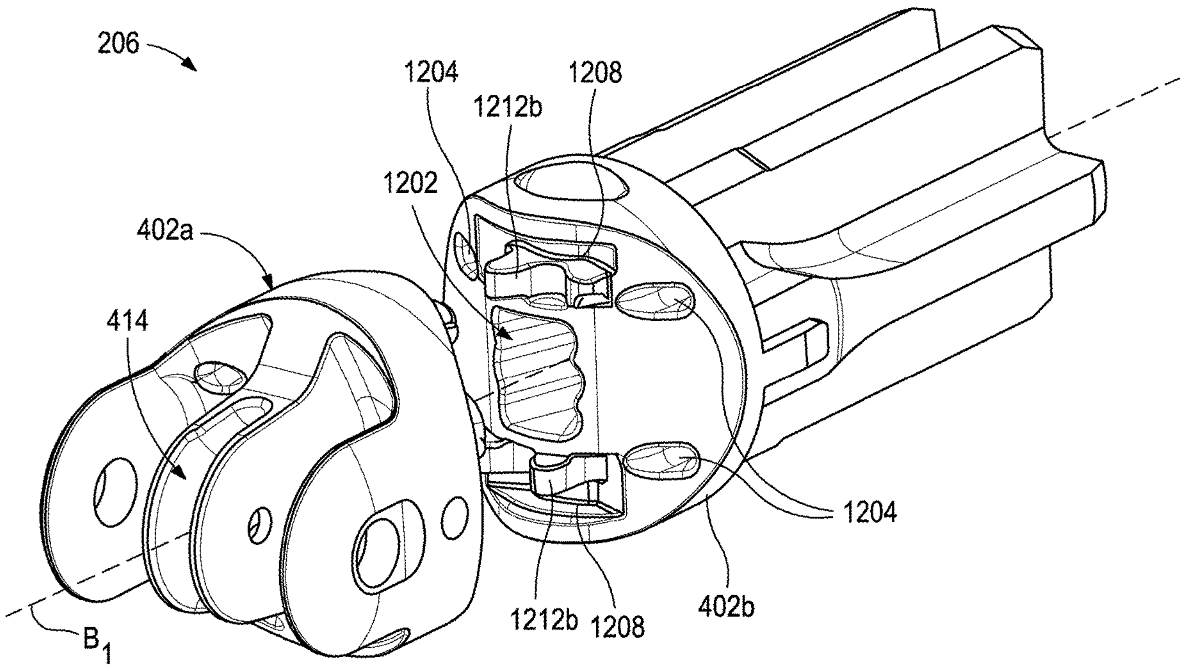
FIGS. 12A and 12B are exploded, isometric views of the distal and proximal clevises of the wrist, as taken from right and left vantage points, according to one or more embodiments.
Figure 12B:
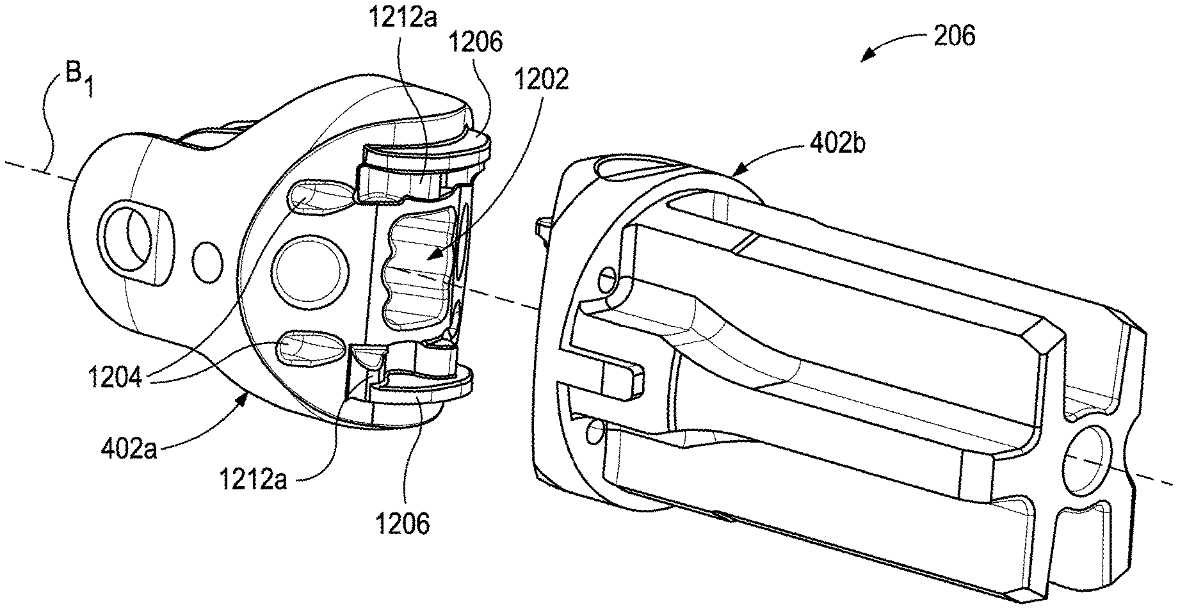

FIGS. 12A and 12B are exploded, isometric views of the distal and proximal clevises 402*a,b* of the wrist 206, as taken from right and left vantage points, according to one or more embodiments. As mentioned above, the proximal end of the distal clevis 402*a* may be rotatably mounted to the distal end of the proximal clevis 402*b*, which allows the wrist 206 to articulate in "yaw" about the first pivot axis $P_1$ (FIG. 4A). As illustrated, both clevises 402*a,b* include or define a central passageway 1202 sized to accommodate the electrical conductors 412*a,b* (FIGS. 4A-4B) and the drive rod 420 (FIGS. 4A-4B). The central passageway 1202 of the distal clevis 402*a* transitions to the central gap 814 provided on the distal end of the distal clevis 402*a*. The distal and proximal clevises 402*a,b* also define a plurality of cable passages 1204 sized to accommodate the drive members 406*a-d* (FIGS. 4A-4B). When the clevises 402*a,b* are rotatably coupled and unarticulated, the central passageways 1202 will axially align to enable the electrical conductors 412*a,b* and the drive rod 420 to extend through the wrist 206, and corresponding cable passages 1204 will axially align to allow the drive members 406*a-d* to extend through the wrist 206.

In the illustrated embodiment, the distal clevis 402*a* may provide and otherwise define one or more camming tabs 1206 (two shown in FIG. 12B) configured to be received within and otherwise mated with one or more corresponding camming slots 1208 (shown in FIG. 12A) defined on the proximal clevis 402*b*. When the clevises 402*a,b* are rotatably coupled, the camming tabs 1206 will be received within the corresponding camming slots 1208, which may help provide vertical joint alignment. In alternative embodiments, the camming tabs 1206 may be provided on the proximal clevis 402*b*, and the camming slots 1208 may be provided on the distal clevis 402*a*, or a combination thereof, without departing from the scope of the disclosure.

In some embodiments, the distal clevis 402*a* may provide and otherwise define one or more first camming surfaces 1210*a* (two shown in FIG. 12B), and the proximal clevis 402B may provide and otherwise define one or more second camming surfaces 1210*b* (two shown in FIG. 12A). The camming surfaces 1210*a,b* may comprise opposing arcuate or curved surfaces. When the clevises 402*a,b* are rotatably coupled, the opposing camming surfaces 1210*a,b* may be in rolling or camming engagement as the wrist 206 articulates. As illustrated, each of the camming surfaces 1210*a,b* are located above or below the instrument axis $B_1$.

In the illustrated embodiment, the distal clevis 402*a* may provide and otherwise define one or more first spur gears 1212*a* (two shown in FIG. 12B), and the proximal clevis 402*b* may provide and otherwise define one or more corresponding second spur gears 1212*b* (two shown in FIG. 12B) configured to interact with the one or more first spur gears 1212*a*. When the clevises 402*a,b* are rotatably coupled, the opposing spur gears 1212*a,b* help the wrist 206 articulate in a controlled manner. As illustrated, the spur gears 1212*a,b* are each located above or below the instrument axis $B_1$, which helps improve rotational backlash and better resist torsional loads. Moreover, in at least one embodiment, the cable passages 1204 may be located in the same plane as the spur gears 1221*a,b*.

Figure 13A:
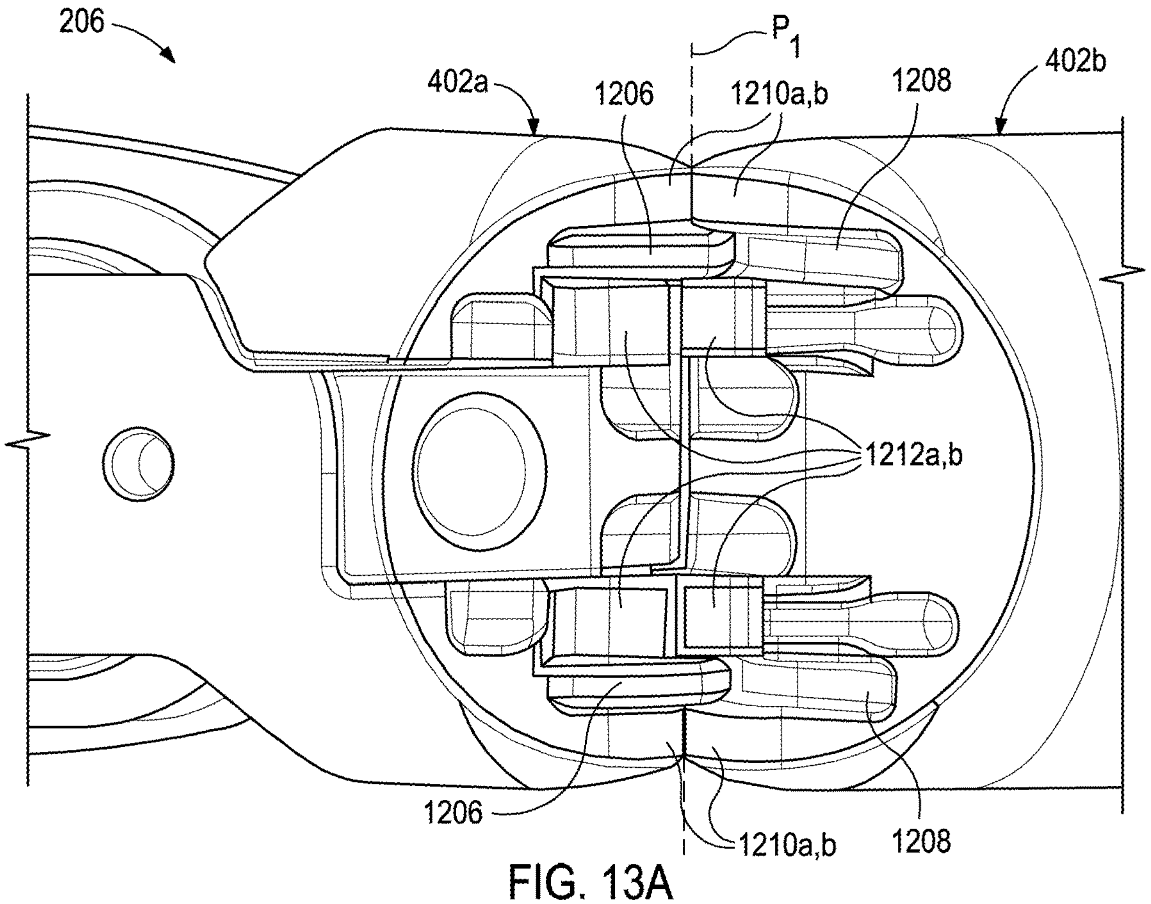
FIG. 13A is an enlarged side view of the wrist of FIGS. 12A-12B, according to one or more embodiments.
Figure 13B:
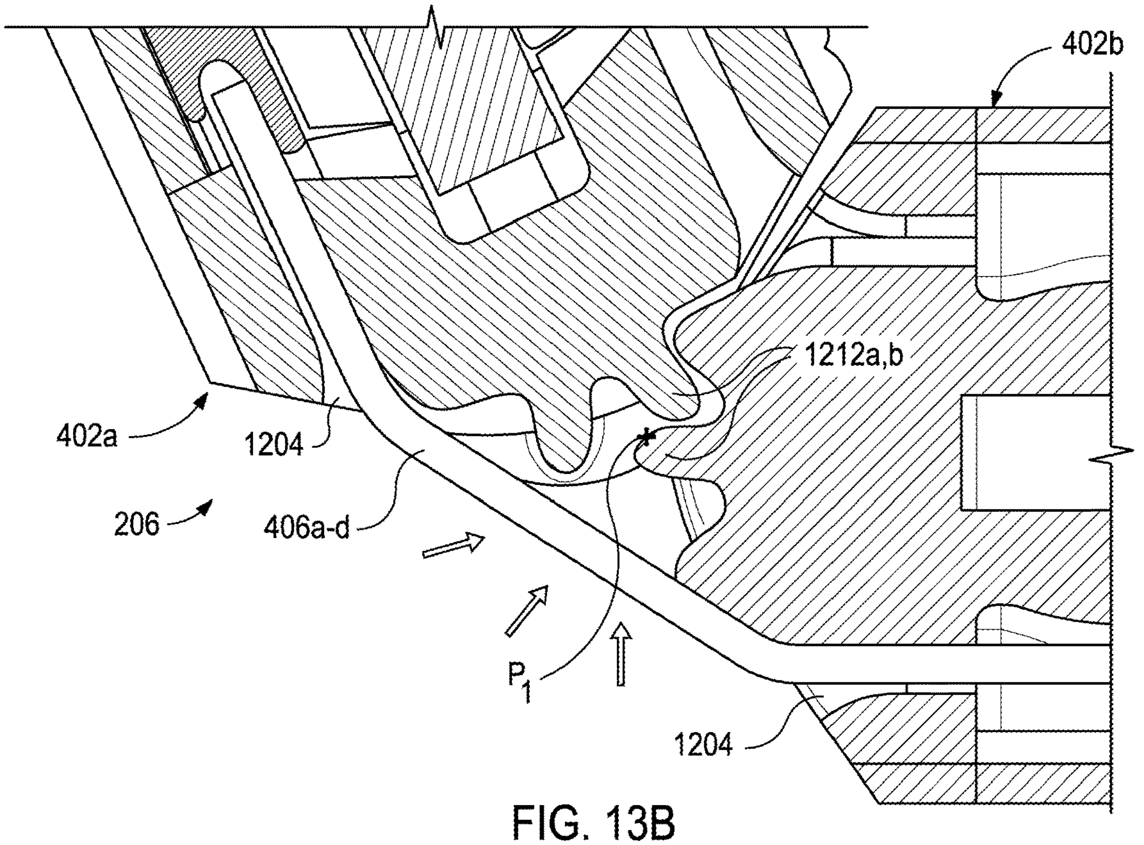
FIG. 13B is a cross-sectional top view of the wrist of FIGS. 12A-12B, according to one or more embodiments.

FIG. 13A is an enlarged side view of the wrist 206 in an articulated state, and FIG. 13B is a cross-sectional top view of the wrist 206 in the articulated state, according to one or more embodiments. In FIG. 13A, the distal clevis 402*a* is rotatably coupled to the proximal clevis 402*b*, thereby providing the first pivot axis $P_1$. As illustrated, the camming tabs 1206 provided by the distal clevis 402*a* are received within and otherwise mated with the corresponding camming slots 1208 provided by the proximal clevis 402*b*. Moreover, the camming surfaces 1210*a,b* are in cammed (rolling) engagement with each other as the wrist 206 articulates about the first pivot axis $P_1$. Furthermore, the spur gears 1212*a,b* are inter-meshed to help provide the wrist 206 with controlled articulation about the first pivot axis $P_1$.

In FIG. 13B, the wrist 206 is shown in an articulated state as the distal clevis 402*a* is rotated relative to the proximal clevis 402*b* about the first pivot axis $P_1$. In the illustrated embodiment one of the drive cables 406*a-d* is shown extended through corresponding cable passages 1204 that allow the drive cable 406*a-d* to extend through the wrist 206. In at least one embodiment, the drive cable 406*a-d* may prove advantageous in blocking tissue from becoming entangled in the intermeshed spur gears 1212*a,b*.

Knife Housing or "Garage"

Figure 14A:
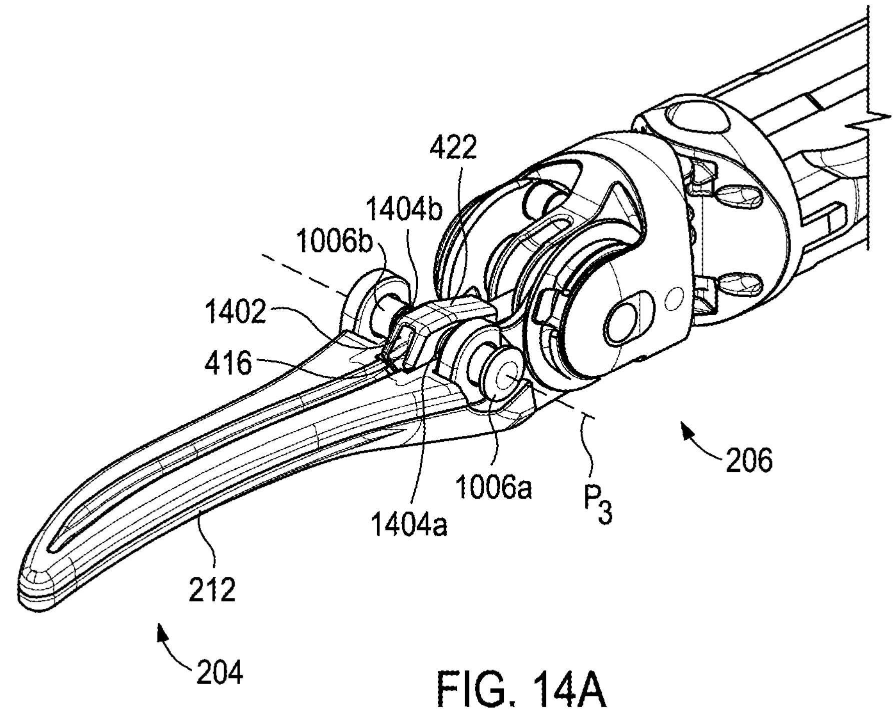
FIG. 14A is another enlarged end view of the end effector, according to one or more additional embodiments.

FIG. 14A is another enlarged isometric view of the end effector 204, according to one or more embodiments of the present disclosure. The upper jaw 210 (FIGS. 2, 4A, 8A-8B, and 9A-9B) is omitted from FIG. 14A to enable viewing of various internal features of the end effector 204 and the wrist 206.

As mentioned above, the knife 416 (mostly occluded) is aligned with and configured to traverse the knife slot 418 defined longitudinally in both the upper and lower jaws 210, 212. The knife housing 422 defines a cavity 1402 sized to receive and "stow" the knife 416 when not in use. The knife 416 is shown in FIG. 14A in a "stowed" position and otherwise received within the cavity 1402. The cavity 1402 provides a conduit through which the drive rod 420 (see FIGS. 15A-15B) is able to extend to move the knife 416 into and along the knife slot 418.

The knife housing 422 may be pivotably mounted to the end effector 204. More particularly, the knife housing 422 may be rotatably mounted between the upper and lower jaws 210, 212 when the jaws 210, 212 are pivotably coupled as described herein with reference to FIGS. 10A-10B. As illustrated, the knife housing 422 may define and otherwise provide opposing first and second bosses 1404*a* and 1404*b* (mostly occluded) that laterally protrude from opposing sides of the knife housing 422. When the jaws 210, 212 are pivotably coupled using the first and second jaw axles 1006*a,b*, as described herein, the bosses 1404*a,b* will be captured between opposing (e.g., upper and lower) portions of the jaws 210, 212, thus axially securing the knife housing 422 at the end effector 204, but simultaneously allowing the knife housing 422 to pivot relative to the jaws 210, 212 about the third pivot axis $P_3$.

Accordingly, the knife housing 422 is not fixed (e.g., immovably secured) to any portion of the end effector 204 or the wrist 206, but is instead pivotably secured between opposing central portions of the jaws 210, 212 when the end effector 204 is assembled. Allowing the knife housing 422 to pivot about the third pivot axis $P_3$ (e.g., due to yaw) may prove advantageous in reducing strain on the knife housing 422 during use.

Figure 14B:
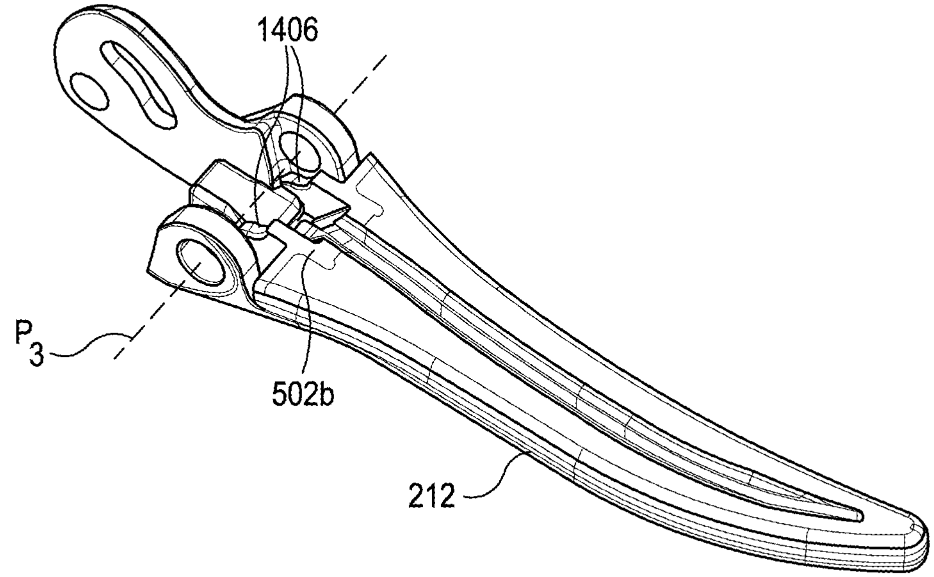
FIG. 14B is an isometric top view of the lower jaw, according to one or more embodiments.

FIG. 14B is an isometric top view of the lower jaw 212, according to one or more embodiments. For purposes of the present discussion, the upper jaw 210 (FIG. 4A) will include similar features. Consequently, the following discussion of the lower jaw 212 will similarly apply to the upper jaw 210.

As indicated above, the knife housing 422 (FIG. 14A) may be pivotably mounted and captured between opposing portions of the jaws 210, 212. As illustrated, the lower jaw 212 includes and otherwise defines one or more arcuate sections 1406 (two shown). In the illustrated embodiment, the arcuate section(s) 1406 are defined by the lower insulator 502*b*, but could alternatively be provided by other portions of the lower jaw 212, without departing from the scope of the disclosure. The upper jaw 210 (FIGS. 2, 4A, 8A-8B, and 9A-9B) provides corresponding arcuate section(s) opposing the arcuate sections(s) 1406 when the jaws 210, 212 are pivotably coupled, as described above with reference to FIGS. 10A-10B. Upon pivotably coupling the jaws 210, 212, the opposing first and second bosses 1404*a,b* (FIG. 14A) of the knife housing 422 (FIG. 14A) will be received between the corresponding arcuate sections 1406 of the upper and lower jaws 210, 212. This will axially secure the knife housing 422 at the end effector 204 (FIG. 14A), while simultaneously allowing the bosses 1404*a,b* to slidingly engage the opposing arcuate sections 1406 as the end effector 204 is articulated in "pitch" about the third pivot axis $P_3$.

Figure 15A:
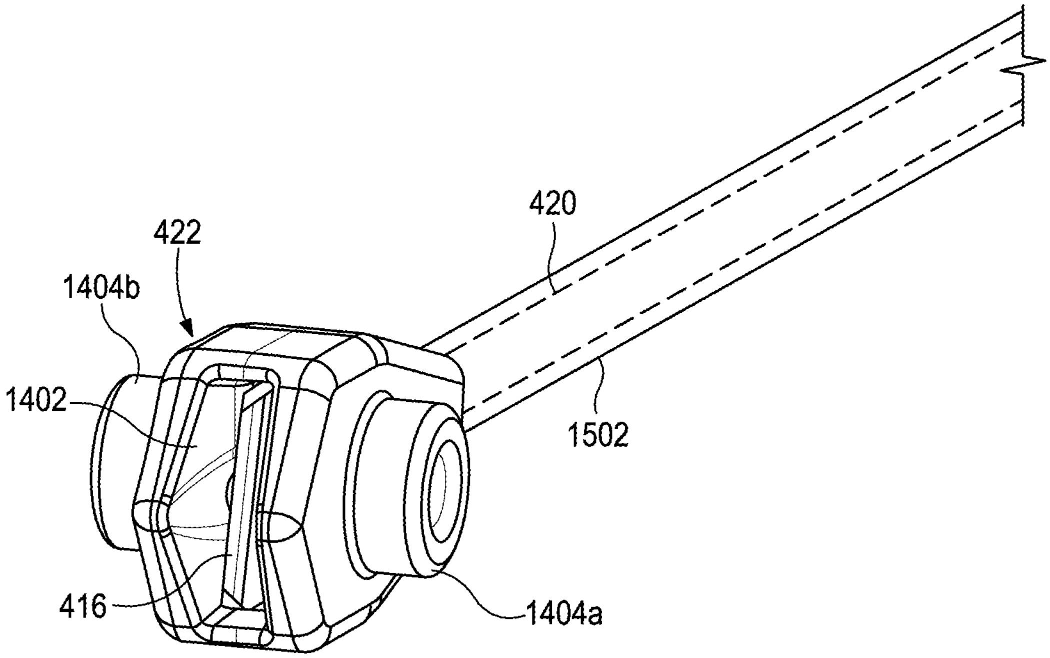
FIGS. 15A and 15B are enlarged isometric views of the knife and the knife housing, according to one or more embodiments.
Figure 15B:
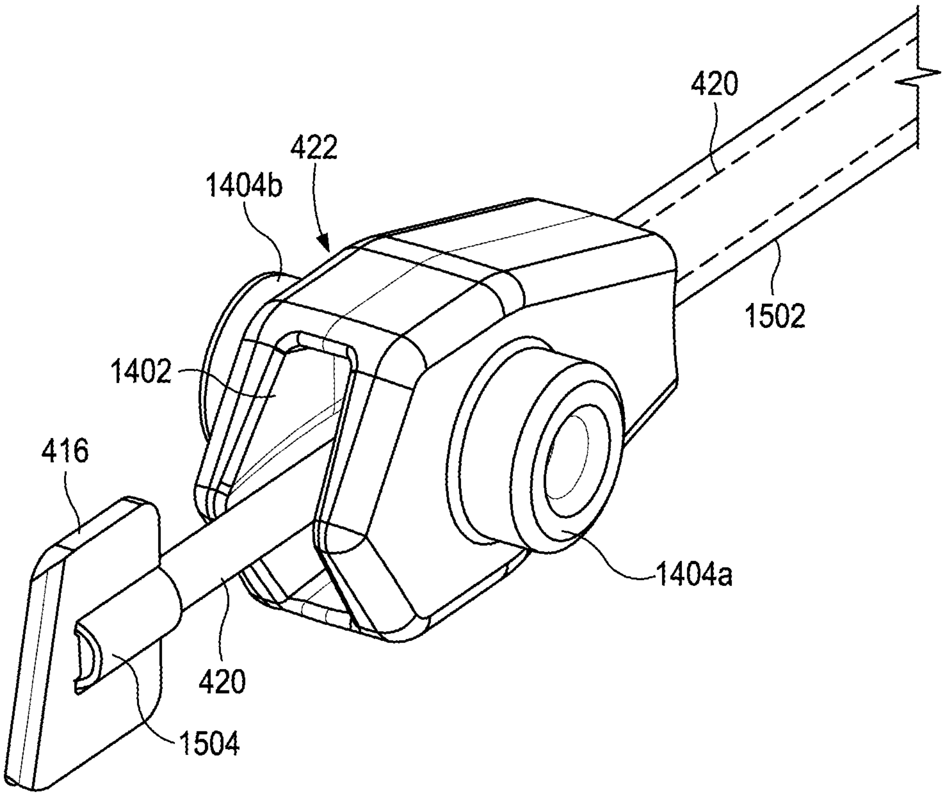

FIGS. 15A and 15B are enlarged isometric views of the knife 416 and the knife housing 422, according to one or more embodiments. In FIG. 15A, the knife 416 is shown in a first or "stowed" position, where the knife 416 is fully received within the cavity 1402 of the knife housing 422. In FIG. 15B, the knife 416 is shown in a second or "extended" position, where the knife 416 is extended distally out of the cavity 1402. FIGS. 15A-15B also more fully depict the first and second bosses 1404*a,b* that laterally protrude from opposing sides of the knife housing 422.

As mentioned above, the knife 416 may be operatively coupled to the distal end of the drive rod 420 (shown in dashed lines in FIG. 15A). In some embodiments, the drive rod 420 may comprise a solid shaft, but may alternatively comprise a tube or tubular structure. Moreover, the drive rod 420 may be made of a variety of flexible materials including, but not limited to, a metal or metal alloy (e.g., a nickel-titanium alloy or "nitinol"), a plastic or thermoplastic material, a composite material, or any combination thereof. The drive rod 420 may also comprise a braided cable construction of a metal (e.g., stainless steel), or any of the aforementioned materials, and such braided cable may be designed and radially constrained to support axial loads.

In some embodiments, as illustrated, a flexible sheath 1502 (e.g., a hypotube or the like) may cover all or a portion of the drive rod 420. The sheath 1502 may support and help prevent buckling of the drive rod 420 upon assuming compressive loads during articulation of the wrist 206 and opening and closure of the jaws 210, 212. Similar to the drive rod 420, the flexible sheath 1502 may be made of a variety of flexible materials including, but not limited to, a metal or metal alloy (e.g., a nickel-titanium alloy or "nitinol"), a metallic coil, a plastic or thermoplastic material, a composite material, or any combination thereof.

Upon firing the end effector 204 (FIG. 14), the drive rod 420 is moved (urged) distally, which correspondingly moves the knife 416 to the extended position and otherwise out of the cavity 1402 and into the knife slot 418 (FIG. 14). As the drive rod 420 translates distally, the sheath 1502 supports the drive rod 420 against axial buckling resulting from compressive loading on the drive rod 420. After firing is complete, the drive rod 420 is retracted proximally, which correspondingly pulls the knife 416 proximally and back to the stowed position and otherwise into the cavity 1402 until it is desired to again fire the end effector 204.

As best seen in FIG. 15B, the knife 416 may be attached to the distal end of the drive rod 420 at a retention feature 1504. The retention feature 1504 may comprise any attachment or coupling means that removably or permanently fixes the knife 416 to the drive rod 420. For example, the retention feature 1504 may comprise, but is not limited to, a welded interface, an adhesive attachment, an interference or shrink fit, an overmold (e.g., a shaped block of material or a support block), one or more mechanical fasteners, or any combination thereof. In at least one embodiment, the retention feature 1504 may comprise a formed shape on the drive rod 420 or alternatively on the knife 416.

Figure 16:
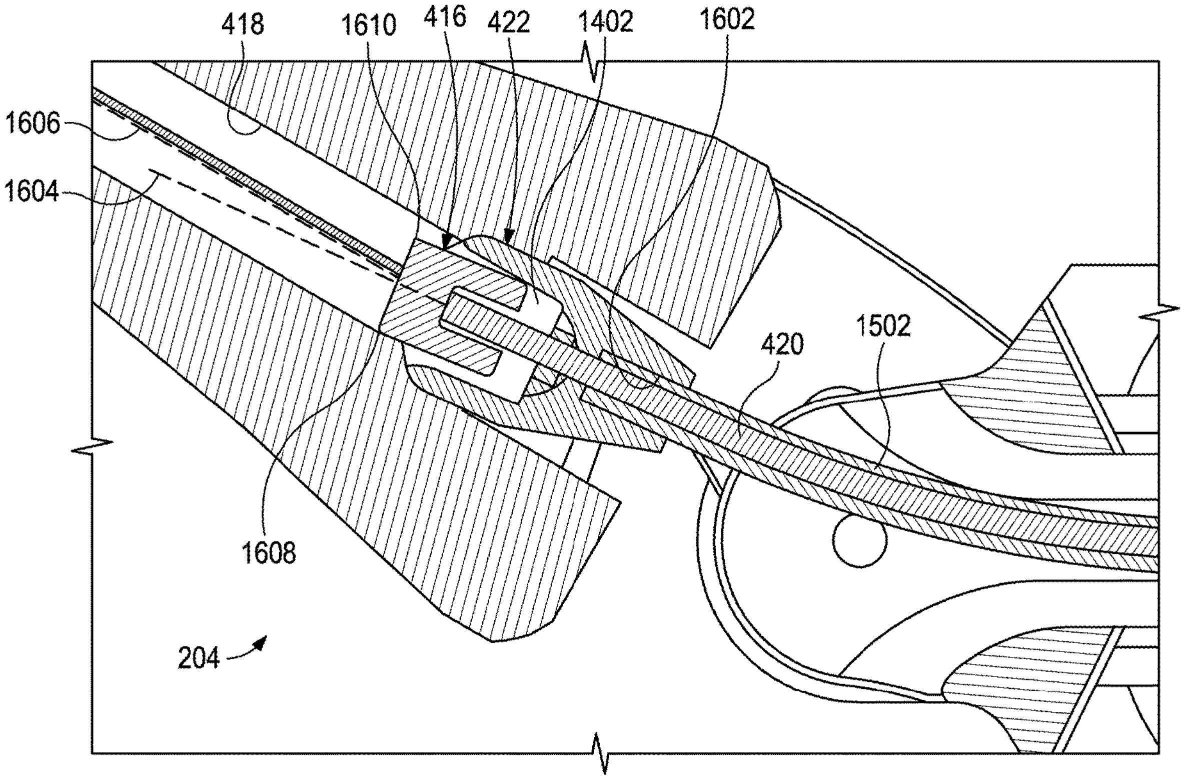
FIG. 16 is an enlarged cross-sectional side view of portions of the end effector and the wrist, according to one or more embodiments.

FIG. 16 is an enlarged cross-sectional side view of portions of the end effector 204 and the wrist 206, according to one or more embodiments. As illustrated, the knife 416 is at least partially received within the cavity 1402 of the knife housing 422, and the drive rod 420 is at least partially received within the flexible sheath 1502.

The knife housing 422 may define a central conduit 1602 that extends to and communicates with the cavity 1402. The drive rod 420 is extendable through the central conduit 1602 and able to translate longitudinally therethrough when transitioning the knife 416 between the stowed and extended positions. In some embodiments, the distal end of the sheath 1502 may be received within the central conduit 1602. In at least one embodiment, for example, the knife housing 422 may be secured to the distal end of the sheath 1502, such as being overmolded onto the sheath 1502. In other embodiments, the knife housing 422 may be secured to the distal end of the sheath 1502 via welding, an adhesive, a shrink-fit or interference engagement, or any combination of the foregoing.

In FIG. 16, the end effector 204 is articulated in pitch and the knife 416 is in the process of transitioning from the stowed position to the extended position. Articulating the end effector 204 also causes the knife housing 422 to pivot about the third pivot axis $P_3$ (FIG. 14), which results in a line of action 1604 (dashed lines) of the drive rod 422 becoming non-parallel to a line of action 1606 (dashed lines) of the knife 416 when the knife 416 exits the knife housing 422 and transitions into the knife slot 418.

In some embodiments, to help ease the transition from the cavity 1402 to the knife slot 418 when the end effector 204 is articulated, at least one of the leading corners 1608, 1610 of the knife 416 may be rounded or chamfered. In the illustrated embodiment, the lower leading corner 1608 of the knife 416 is rounded, while the upper leading corner 1610 defines a sharp angle. As will be appreciated, the rounded, lower leading corner 1608 may prove advantageous in creating a smooth sliding transition for the knife 416 as it enters the knife track 418.

In other embodiments, the lower leading corner 1608 may define a sharp angle, and the upper leading corner 1610 may alternatively be rounded or chamfered. In yet other embodiments, both leading corners 1608, 1610 may be rounded or chamfered, without departing from the scope of the disclosure.

As illustrated, the drive rod 420 is directly pushed without any redirect pulleys being used in the end effector 204. Those skilled in the art will readily appreciate that this can simplify the proximal end of the wrist 206 and the instrument as a whole, which can reduce costs.

Figure 17:
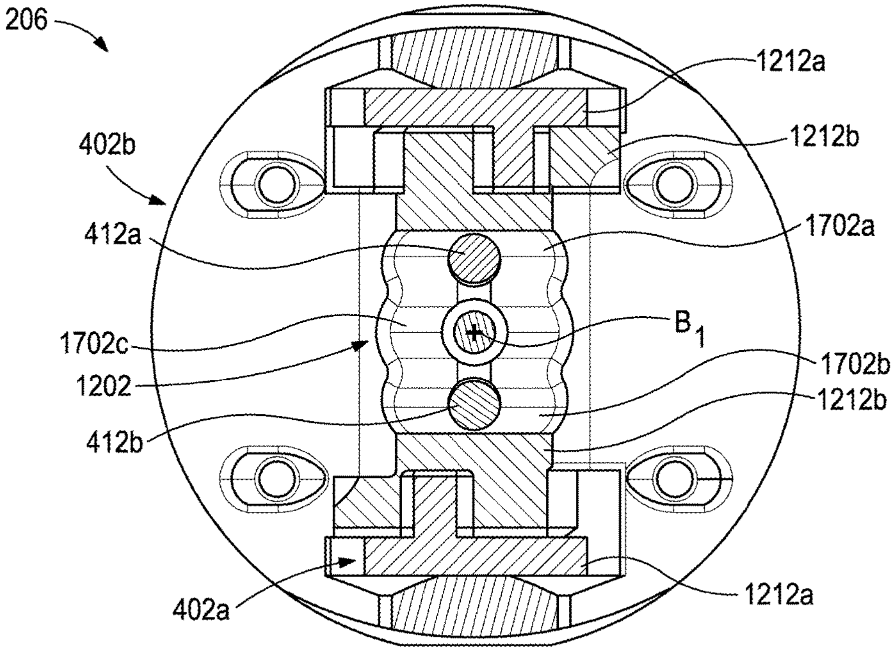
FIG. 17 is a cross-sectional end view of the wrist as taken through the first pivot axis, according to one or more embodiments.

FIG. 17 is a cross-sectional end view of the wrist 206 as taken through the first pivot axis $P_1$ (FIG. 4A), according to one or more embodiments. As discussed above, the proximal end of the distal clevis 402*a* is rotatably mounted to the distal end of the proximal clevis 402*b* at the first pivot axis $P_1$, which allows the wrist 206 to articulate in "yaw" about the first pivot axis $P_1$. A cross-section of the first spur gears 1212*a* of the distal clevis 402*a* are shown intermeshed with a cross-section of the second spur gears 1212*b* of the proximal clevis 402*b*, as generally described above.

Also shown in FIG. 17 is the central passageway 1202 of the proximal clevis 402*b*, which is sized to accommodate the electrical conductors 412*a,b* and the drive rod 420. While not shown, a similar central passageway may be defined in the distal clevis 402*a* and may axially align with the central passageway 1202 of the proximal clevis 402*b*. In some embodiments, as illustrated, the central passageway 1202 may flare open and define one or more arcuate transition surfaces, shown as a first arcuate transition surface 1702*a*, a second arcuate transition surface 1702*b*, and a third arcuate transition surface 1702*c*. The arcuate transition surfaces 1702*a-c* may be configured to receive and engage the electrical conductors 412*a,b* and the drive rod 420 as the wrist 206 articulates in "yaw" about the first pivot axis $P_1$. The arcuate transition surfaces 1702*a-c* may prove advantageous in providing a smooth and curved transition for the electrical conductors 412*a,b* and the drive rod 420 as the wrist 206 articulates in "yaw," as opposed to sharp transition surfaces, which could fatigue the material of the electrical conductors 412*a,b* and the drive rod 420 over time.

As illustrated, the drive rod 420 extends along the instrument axis $B_1$, and the electrical conductors 412*a,b* are arranged on radially opposite sides (e.g., above and below) of the drive rod 420. In the illustrated embodiment, the electrical conductors 412*a,b* are arranged above and below the drive rod 420, but could alternatively be arranged on opposing left and right sides of the drive rod 420, without departing from the scope of the disclosure. Accordingly, the drive rod 420 may be centered (centrally-located) relative to the cross-section of the wrist 206, which can help ensure that the controls length compensation is symmetric and the parasitic load imparted on the articulation system is symmetric, such that clamp force variation relative to a particular pose of the end effector 204 is consistent and predictable.

Figure 18:
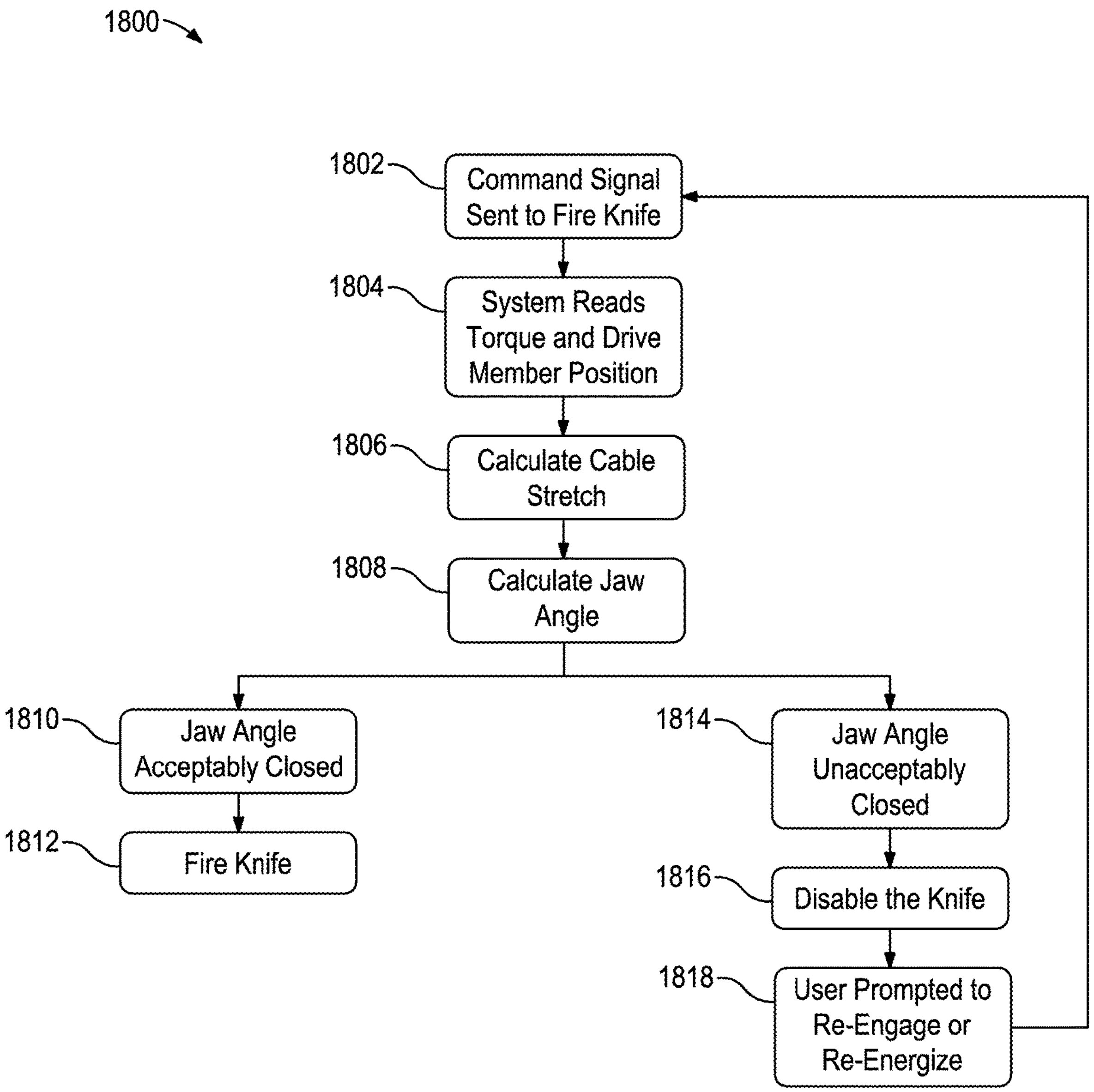
FIG. 18 is a schematic flowchart of an example process algorithm, according to one or more embodiments of the present disclosure.

FIG. 18 is a schematic flowchart of an example process algorithm 1800 in accordance with one or more embodiments of the present disclosure. The process algorithm 1800 may be used to infer jaw position based on closure cable position and load, which can ensure that the tips of the jaws 210, 212 are fully approximated and at an angle safe for firing. As will be appreciated, this can help prevent the knife 416 from escaping the knife slot 418 in an over-stuffed jaw condition.

As shown in the process algorithm 1800, a user sends a command signal to request firing of the knife 416, as at 1802. The user may send the command signal to the robotic surgical system 100 (FIG. 1), for example, and more particularly, to the control computer 104 (FIG. 1). The system will read the torque and the position of the drive members in preparation for closure of the jaws 210, 212, as at 1804. Based on the measured torque, the system will calculate cable stretch, as at 1806, and based on the calculated cable length, and the actuator position relative to home, the position of the jaws 210, 212 (the real aperture angle between the two jaws 210, 212) may then be calculated by the system, as at 1808. If the jaw angle between the jaws 210, 212 is determined to be acceptably closed, as at 1810, then the system will proceed to fire the knife 416, as at 1812.

If, however, the jaw angle between the jaws 210, 212 is determined to be un-acceptably closed, as at 1814, the system may be programmed to disable the knife 416, as at 1816. As will be appreciated, if the knife 416 were to be fired (extended along the knife slot 418) with the jaws 210, 212 open past a predetermined angle, the knife 416 could be completely exposed and potentially dislodge from the knife slot 418. Upon disablement of the knife 416, the user may then be prompted to reengage the tissue between the jaws 210, 212 or re-energize the electrodes 414*a,b*, as at 1818. The process algorithm 1800 may then return to the first step, as at 1802, and the process will repeat itself.

Embodiments disclosed herein include:

A. An end effector for a surgical tool includes opposing first and second jaws rotatably coupled to each other at a jaw pivot axis, a knife slot defined in one or both of the first and second jaws, a knife coupled to a distal end of a drive rod and longitudinally extendable into the knife slot, and a knife housing pivotably coupled between the first and second jaws at the jaw pivot axis and defining a cavity sized to receive the knife, wherein the drive rod is actuatable to move the knife between a stowed position, where the knife is received within the cavity, and an extended position, where the knife is extended out of the cavity and into the knife slot.

B. A surgical tool includes a drive housing and an elongate shaft extending from the drive housing, a wrist coupled to a distal end of the shaft, an end effector rotatably coupled to the wrist and including opposing first and second jaws rotatably coupled to each other at a jaw pivot axis, a knife slot defined in one or both of the first and second jaws, a drive rod extending from the drive housing and through the wrist, a knife coupled to a distal end of the drive rod and longitudinally extendable into the knife slot, and a knife housing pivotably coupled between the first and second jaws at the jaw pivot axis and defining a cavity sized to receive the knife, wherein the drive rod is actuatable from the drive housing to move the knife between a stowed position, where the knife is received within the cavity, and an extended position, where the knife is extended out of the cavity and into the knife slot.

Each of embodiments A and B may have one or more of the following additional elements in any combination: Element 1: wherein the knife housing provides opposing first and second bosses laterally protruding from opposing sides of the knife housing, and wherein the first and second bosses are captured between opposing portions of the jaws at the jaw pivot axis. Element 2: wherein capturing the first and second bosses between the opposing portions of the first and second jaws axially secures the knife housing at the end effector while simultaneously allowing the knife housing to pivot about the jaw pivot axis. Element 3: wherein the first jaw provides one or more first arcuate sections and the second jaw provides one or more second arcuate sections, and wherein the first and second bosses are pivotably mounted between the one or more first arcuate sections and the one or more second arcuate sections. Element 4: wherein the first jaw includes a first electrode and a first insulator secured thereto, and the second jaw includes a second electrode and a second insulator secured thereto, and wherein the one or more first arcuate sections are defined by the first insulator and the one or more second arcuate sections are defined by the second insulator. Element 5: wherein the first jaw defines first and second jaw axle apertures, and the second jaw defines first and second jaw axle apertures, the end effector further comprising a first jaw axle received within the first jaw axle apertures of the first and second jaws, and a second jaw axle received within the second jaw axle apertures of the first and second jaws, the first and second jaw axles extending co-axially with the first and second bosses along the jaw pivot axis. Element 6: wherein the drive rod is made of a flexible material selected from the group consisting of a metal, a metal alloy, a plastic, a thermoplastic, a composite material, a braided cable, and any combination thereof. Element 7: wherein the knife housing defines a central conduit that extends to and communicates with the cavity to allow the drive rod translate through the knife housing. Element 8: further comprising a sheath covering at least a portion of the drive rod to prevent buckling of the drive rod, wherein a distal end of the sheath is received within the central conduit. Element 9: wherein the knife housing is secured to the sheath by at least one of overmolding, welding, an adhesive, a shrink fit engagement, and any combination thereof. Element 10: wherein the sheath is made of a flexible material selected from the group consisting of a metal, a metal alloy, a metallic coil, a plastic, a thermoplastic, a composite material, and any combination thereof. Element 11: wherein the knife is attached to a distal end of the drive rod at a retention feature selected from the group consisting of a welded interface, an adhesive attachment, an interference or shrink fit, an overmold, one or more mechanical fasteners, and any combination thereof. Element 12: wherein the knife provides upper and lower leading corners, and wherein at least one of the upper and lower leading corners is rounded or chamfered.

Element 13: further comprising first and second electrical conductors extending from the drive housing and through the wrist, the first electrical conductor terminating at a first electrode coupled to the first jaw and the second electrical conductor terminating at a second electrode coupled to the second jaw, wherein the drive rod is centrally located within the wrist and the electrical conductors are arranged on radially opposite sides of the drive rod. Element 14: wherein the wrist includes a proximal clevis and a distal clevis rotatably mounted to the proximal clevis, and wherein at least one of the proximal and distal clevises defines a central passageway sized to accommodate the first and second electrical conductors and the drive rod. Element 15: wherein the knife housing provides opposing first and second bosses laterally protruding from opposing sides of the knife housing, and wherein the first and second bosses are captured between opposing portions of the jaws that axially secure the knife housing at the end effector while simultaneously allowing the knife housing to pivot about the jaw pivot axis. Element 16: wherein the first jaw provides one or more first arcuate sections and the second jaw provides one or more second arcuate sections, and wherein the first and second bosses are pivotably mounted between the one or more first arcuate sections and the one or more second arcuate sections. Element 17: wherein the first jaw defines first and second jaw axle apertures, and the second jaw defines first and second jaw axle apertures, the surgical tool further comprising a first jaw axle received within the first jaw axle apertures of the first and second jaws, and a second jaw axle received within the second jaw axle apertures of the first and second jaws, the first and second jaw axles extending co-axially with the first and second bosses and along the jaw pivot axis. Element 18: wherein the knife provides upper and lower leading corners, and wherein at least one of the upper and lower leading corners is rounded or chamfered.

By way of non-limiting example, exemplary combinations applicable to A and B include: Element 1 with Element 2; Element 1 with Element 3; Element 2 with Element 4; Element 1 with Element 5; Element 7 with Element 8; Element 8 with Element 9; Element 8 with Element 10; Element 13 with Element 14; and Element 15 with Element 16.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

What is claimed is:

1. An end effector for a surgical tool, comprising:
- opposing first and second jaws each defining a first jaw axle aperture;
- a knife slot defined in one or both of the first and second jaws;
- a knife coupled to a distal end of a drive rod and longitudinally extendable into the knife slot;
- a knife housing defining a cavity sized to receive the knife, wherein the knife housing provides a first boss laterally protruding from a first side of the knife housing; and
- a first jaw axle extending through the first jaw axle aperture of each jaw and mounted to the first boss, thereby rotatably coupling the first jaw, the second jaw, and the knife housing together at a pivot axis,
- wherein the drive rod is actuatable to move the knife between a stowed position, where the knife is received within the cavity, and an extended position, where the knife is extended out of the cavity and into the knife slot.

2. The end effector of claim 1, wherein the knife housing further provides a second boss laterally protruding from a second side of the knife housing opposite the first side, wherein the first and second bosses are captured between opposing first and second portions of the first and second jaws at the jaw pivot axis, and wherein the first portions define the first jaw axle apertures.

3. The end effector of claim 2, wherein capturing the first and second bosses between the opposing first and second portions of the first and second jaws axially secures the knife housing at the end effector while simultaneously allowing the knife housing to pivot about the jaw pivot axis.

4. The end effector of claim 2, wherein the first jaw provides one or more first arcuate sections and the second jaw provides one or more second arcuate sections, and wherein the first and second bosses are pivotably mounted between the one or more first arcuate sections and the one or more second arcuate sections.

5. The end effector of claim 4, wherein the first jaw includes a first electrode and a first insulator secured thereto, and the second jaw includes a second electrode and a second insulator secured thereto, and wherein the one or more first arcuate sections are defined by the first insulator and the one or more second arcuate sections are defined by the second insulator.

6. The end effector of claim 2, wherein the first and second jaws each further define a second jaw axle aperture, the end effector further comprising:
- a second jaw axle extending through the second jaw axle apertures and mounted to the second boss, the first and second jaw axles extending co-axially with the first and second bosses along the jaw pivot axis.

7. The end effector of claim 1, wherein the drive rod is made of a material selected from the group consisting of a metal, a metal alloy, a plastic, a thermoplastic, a composite material, a braided cable, and any combination thereof.

8. The end effector of claim 1, wherein the knife housing defines a central conduit that extends to and communicates with the cavity to allow the drive rod to translate through the knife housing.

9. The end effector of claim 8, further comprising a sheath covering at least a portion of the drive rod to prevent buckling of the drive rod, wherein a distal end of the sheath is received within the central conduit.

10. The end effector of claim 9, wherein the knife housing is secured to the sheath by at least one of overmolding, welding, an adhesive, a shrink fit engagement, and any combination thereof.

11. The end effector of claim 1, wherein the knife provides upper and lower leading corners, and wherein at least one of the upper and lower leading corners is rounded or chamfered.

12. The surgical tool of claim 11, wherein only one of the upper and lower leading corners is rounded or chamfered.

13. A surgical tool, comprising:
- a drive housing and an elongate shaft extending from the drive housing;
- a wrist coupled to a distal end of the shaft; and
- an end effector rotatably coupled to the wrist and including:
  - opposing first and second jaws that each define a first jaw axle aperture;
  - a knife slot defined in one or both of the first and second jaws;
  - a drive rod extending from the drive housing and through the wrist;
  - a knife coupled to a distal end of the drive rod and longitudinally extendable into the knife slot;
  - a knife housing pivotably coupled between the first and second jaws at the jaw pivot axis and defining a cavity sized to receive the knife, wherein the knife housing provides a first boss laterally protruding from a first side of the knife housing; and
  - a first jaw axle extending through the first jaw axle apertures and mounted to the first boss, thereby rotatably coupling the first jaw, the second jaw, and the knife housing together at a pivot axis,
- wherein the drive rod is actuatable from the drive housing to move the knife between a stowed position, where the knife is received within the cavity, and an extended position, where the knife is extended out of the cavity and into the knife slot.

14. The surgical tool of claim 13, further comprising first and second electrical conductors extending from the drive housing and through the wrist, the first electrical conductor terminating at a first electrode coupled to the first jaw and the second electrical conductor terminating at a second electrode coupled to the second jaw,
- wherein the drive rod is centrally located within the wrist and the electrical conductors are arranged on radially opposite sides of the drive rod.

15. The surgical tool of claim 14, wherein the wrist includes a proximal clevis and a distal clevis rotatably mounted to the proximal clevis, and wherein at least one of the proximal and distal clevises defines a central passageway sized to accommodate the first and second electrical conductors and the drive rod.

16. The surgical tool of claim 13, wherein the knife housing further provides a second boss laterally protruding from a second side of the knife housing opposite the first side, wherein the first and second bosses are captured between opposing first and second portions of the first and second jaws that axially secure the knife housing at the end effector while simultaneously allowing the knife housing to pivot about the jaw pivot axis, and wherein the first portions define the first jaw axle apertures.

17. The surgical tool of claim 16, wherein the first jaw provides one or more first arcuate sections and the second jaw provides one or more second arcuate sections, and wherein the first and second bosses are pivotably mounted between the one or more first arcuate sections and the one or more second arcuate sections.

18. The surgical tool of claim 17, wherein the first and second jaws each further define a second jaw axle aperture, the surgical tool further comprising:

a second jaw axle extending through the second jaw axle apertures and mounted to the second boss, the first and second jaw axles extending co-axially with the first and second bosses and along the jaw pivot axis.

19. The surgical tool of claim 13, wherein the knife provides upper and lower leading corners, and wherein at least one of the upper and lower leading corners is rounded or chamfered.

20. A surgical tool, comprising:

opposing first and second jaws that each define a jaw axle aperture;

a knife housing defining a cavity and providing a boss;

a knife movable between a stowed position, in which the knife is arranged in the cavity, and an extended position, in which the knife is arranged outside of the cavity; and a jaw axle extending through the jaw axle apertures and mounted to the boss, thereby rotatably coupling the first jaw, the second jaw, and the knife housing together at a pivot axis.

* * * * *